US011213433B2

(12) United States Patent
Janot et al.

(10) Patent No.: US 11,213,433 B2
(45) Date of Patent: Jan. 4, 2022

(54) CARPAL TUNNEL WRIST BRACE

(71) Applicant: DJO FRANCE, Mouguerre (FR)

(72) Inventors: Vincent Janot, Cambo-les-bains (FR); Julien Oxoteguy, Cambo-les-bains (FR)

(73) Assignee: DJO FRANCE, Mouguerre (FR)

( * ) Notice: Subject to any disclaimer, the term of this patent is extended or adjusted under 35 U.S.C. 154(b) by 251 days.

(21) Appl. No.: 16/557,063

(22) Filed: Aug. 30, 2019

(65) Prior Publication Data

US 2020/0069480 A1 Mar. 5, 2020

Related U.S. Application Data

(60) Provisional application No. 62/790,620, filed on Jan. 10, 2019, provisional application No. 62/726,130, filed on Aug. 31, 2018.

(51) Int. Cl.
*A61F 5/00* (2006.01)
*A61F 13/00* (2006.01)
*A61F 13/10* (2006.01)

(52) U.S. Cl.
CPC .................................. *A61F 13/107* (2013.01)

(58) Field of Classification Search
USPC ........................................................ D24/190
See application file for complete search history.

(56) References Cited

U.S. PATENT DOCUMENTS

| | | | | |
|---|---|---|---|---|
| 3,938,509 A * | 2/1976 | Barber | ................ | A61F 5/05866 602/21 |
| 4,677,971 A * | 7/1987 | Lindemann | ............. | A61F 5/013 473/62 |
| 4,883,073 A * | 11/1989 | Aziz | ..................... | A61F 5/0118 128/878 |
| 5,713,837 A * | 2/1998 | Grim | ...................... | A61F 5/0111 602/21 |
| 5,766,141 A * | 6/1998 | Gould | ................... | A61F 13/108 602/20 |
| 7,922,680 B2 * | 4/2011 | Nordt, III | ............. | A41D 13/088 602/21 |

(Continued)

FOREIGN PATENT DOCUMENTS

| | | | | |
|---|---|---|---|---|
| WO | WO-0217827 A1 * | 3/2002 | ............. | A61F 5/0118 |
| WO | WO-2006084220 A2 * | 8/2006 | ............. | A61F 5/028 |

(Continued)

OTHER PUBLICATIONS

International Search Report and Written Opinion dated Oct. 29, 2019 in application No. PCT/US2019/048014.

*Primary Examiner* — Kim M Lewis
(74) *Attorney, Agent, or Firm* — Knobbe Martens Olson & Bear LLP

(57) ABSTRACT

A brace for treating or preventing carpal tunnel injury includes a body having a proximal end and a distal end. The body includes a forearm support at the proximal end and a wrist support coupled to the forearm support by a neck portion. The wrist support includes a first palmar strap support. A first member and a second member extend from the wrist support towards the distal end. The body also includes a distal palmar support, a proximal palmar aperture, a palm band having a second palmar strap support, and a palmar strap. The palmar strap extends across a portion of the back of the hand and over a purlicue of the hand.

20 Claims, 16 Drawing Sheets

(56) References Cited

U.S. PATENT DOCUMENTS

| | | | |
|---|---|---|---|
| 2005/0240140 A1 | 10/2005 | Nelson et al. | |
| 2007/0100266 A1 | 5/2007 | Hargrave et al. | |
| 2010/0298750 A1* | 11/2010 | Chiang | A61F 5/0118 602/21 |
| 2011/0066095 A1* | 3/2011 | Price | A61F 5/0102 602/16 |
| 2013/0211305 A1 | 8/2013 | Heffernan | |
| 2014/0121579 A1 | 5/2014 | Hinds | |
| 2017/0065448 A1* | 3/2017 | Michell | A61F 5/013 |
| 2018/0110643 A1* | 4/2018 | Carlson | A61F 5/05866 |
| 2018/0289522 A1* | 10/2018 | Zhu | A61F 5/012 |

FOREIGN PATENT DOCUMENTS

| | | | |
|---|---|---|---|
| WO | WO 18/136748 | 7/2018 | |
| WO | WO-2018206903 A1 * | 11/2018 | A61F 5/0118 |

* cited by examiner

| 168 | ↕ 168h |
| 170 | ↕ 170h |
| 172 | ↕ 172h |
| 174 | ↕ 174h |

*FIG. 7*

CARPAL TUNNEL WRIST BRACE

FIELD

This disclosure relates to orthopedic braces. In particular, a carpal tunnel wrist brace is disclosed.

BACKGROUND

Carpal tunnel syndrome is a condition that causes numbness, tingling and other symptoms in the hand and arm. Carpal tunnel syndrome is caused by pressure on the median nerve. The median nerve runs from your forearm through a passageway in your wrist (carpal tunnel) to your hand. It provides sensation to the palm side of your thumb and fingers, except the little finger. It also provides nerve signals to move the muscles around the base of your thumb (motor function). Positions of extreme wrist flexion and extension are known to increase pressures within the carpal canal and apply pressure on the nerve.

The anatomy of your wrist, health problems and possibly repetitive hand motions can contribute to carpal tunnel syndrome. The first symptoms often include numbness or tingling in your thumb, index and middle fingers that comes and goes. Carpal tunnel syndrome may also cause discomfort in your wrist and the palm of your hand, and when severe, maybe treated through surgery.

Although typically performed on an outpatient basis, recovery from carpal tunnel surgery can be lengthy. Pain, swelling, and stiffness after the procedure are common. Minor soreness in your palm may last for several weeks to several months. Grip and pinch strength usually return by about two to three months after surgery. Common complications of carpal tunnel release surgery include bleeding, infection, and nerve aggravation or injury. Accordingly, it would be advantageous to be able to prevent or treat a carpal tunnel injury or inflammation to avoid the recovery time and risks of surgery.

SUMMARY OF CERTAIN EMBODIMENTS

The systems, methods, and devices of the invention each have several aspects (features), no single aspect of which is solely responsible for its desirable attributes. Without limiting the scope of this invention as expressed by the claims which follow, some of the aspects are described below. Also, various features of the embodiments described below maybe included on a brace to alleviate or prevent carpal tunnel injury. The drawings referred to in this disclosure illustrate various features that can be included in various implementations or examples of a brace. In some examples, not all of the features in a figure are included in a particular implementation of a brace. Various implementations of a brace can also have additional features.

In one innovation, a brace for carpal tunnel injury includes a body having a proximal end and a distal end defining s longitudinal direction, the body having a forearm support at the body proximal end, a wrist support coupled to the forearm support by a neck portion, the wrist support comprising a first palmar strap support disposed on a lateral side of the wrist support, and a first member and a second member extending from the wrist support in the longitudinal direction towards the distal end. The brace further includes a distal palmar support coupled to the wrist support by the first and second member, a proximal palmar aperture surrounded by the wrist support, the first and second members and the palm support, the proximal palmar aperture configured to fit over a portion of the proximal palmer of a hand, a palm band coupled to the first member at a proximal end and extending laterally from the first member to a distal end, the palm band comprising a second palmar strap support at the palm band distal end, the palm band configured to extend from the first member across a portion of the back of the hand when the brace is worn, and a palmar strap, extending between a proximal end attached to the first palmar strap support to a distal end, the palmer strap configured to extend through the second palmer strap support across a portion of the back of the hand and over a purlicue of the hand, the distal end of the palmar strap configured to removably attach to the distal palmar support.

The brace may have one or more other aspects (or features), certain aspects being noted here. However, various embodiments of the acetabular cup assembly may have additional aspects or fewer aspects, and the aspects disclosed herein can be used together in an number of embodiments even if specifically not illustrated or described as being in a certain embodiment, as one of ordinary skill in the art will appreciate.

In some embodiments, the brace further includes a first wrist strap support and a second wrist strap support arranged on opposite lateral sides of the wrist support, and a wrist strap having a proximal end attached to the first wrist strap support, a distal end of the wrist strap configured to extend through the second wrist strap support and removably attach to a portion of the brace to secure the wrist support to a hand when the brace is worn. In some embodiments, the portion of the brace the distal end of the wrist strap removably attaches to is the wrist strap. In some embodiments, the first palmer strap support comprises an elongated first and second slot, and wherein the proximal end of the palmar strap passes through the first and second slot to attach to the first palmar support.

In some embodiments, the brace further includes a first wrist strap support on a lateral side of the wrist support, the first wrist strap support having an elongated slot configured to receive a wrist strap, the first palmer strap support being aligned on the same lateral side of the wrist support as the first wrist strap support, and the first palmer strap support includes an elongated first and second slot aligned in parallel, and the elongated slot of the first wrist strap support is aligned at an angle with the first and second slots of the first palmer strap support such that the elongated slot of the first wrist strap support is not aligned parallel to the first and second slots of the first palmer strap support.

In some embodiments of the brace, the elongated slot of the first wrist strap support is disposed distal to the longitudinal axis of the brace relative to the first and second slots of the first palmer strap support. In some embodiments, the brace further includes a first forearm strap support and a second forearm strap support arranged on opposite lateral sides of the forearm support, and a forearm strap having a proximal end attached to the first forearm strap support, a distal end of the forearm strap configured to extend through the second forearm strap support and removably attach to a portion of the brace to secure the forearm support to a forearm when the brace is worn. In some embodiments, the distal end of the forearm strap removably attaches to the forearm strap. In some embodiments, the distal end of the forearm strap removably attaches to a fastening surface on the brace. In some embodiments the fastening surface is a fabric.

In some embodiments of the brace, the brace further includes a distal exterior layer on the surface of the brace facing away from the hand when the brace is worn. In some embodiments, the first layer is rubber. In some embodiments, the brace further includes a proximal exterior layer on the surface of the brace facing towards the hand when the brace is worn. In some embodiments, the proximal exterior layer is a fabric. In some embodiments, the brace further includes a semi-rigid layer disposed between the distal exterior layer and the proximal exterior layer. In some embodiments, the semi-rigid layer comprises metal, plastic, a composite material, that is stiff to provide support but at least slightly deformable when enough force is applied to it. For example, in some embodiments the semi-rigid material is metal having a thickness of between about 0.4 mm and 2.7 mm. In some embodiments, the brace further comprises a fastener layer disposed between the distal exterior layer and the semi-rigid layer, wherein the distal exterior layer includes at least one cutout that exposes a portion of the fastener layer. In some embodiments the fastener layer is configured such that a portion of at least one strap of the brace may removably attach to a portion of the fastener layer exposed in a cutout of the distal exterior layer.

BRIEF DESCRIPTION OF THE DRAWINGS

The features and advantages of the braces and methods described herein will become more fully apparent from the following description and appended claims, taken in conjunction with the accompanying drawings. These drawings depict only several embodiments in accordance with the disclosure and are not to be considered limiting of its scope. In the drawings, similar reference numbers or symbols typically identify similar components, unless context dictates otherwise. In some instances, the drawings may not be drawn to scale.

FIG. 7 is a cross-sectional view schematic of an example of the layers of the CTW brace 100 of FIG. 1A along line $L_1$-$L_1$.

DETAILED DESCRIPTION OF CERTAIN INVENTIVE ASPECTS

Figure 1A:
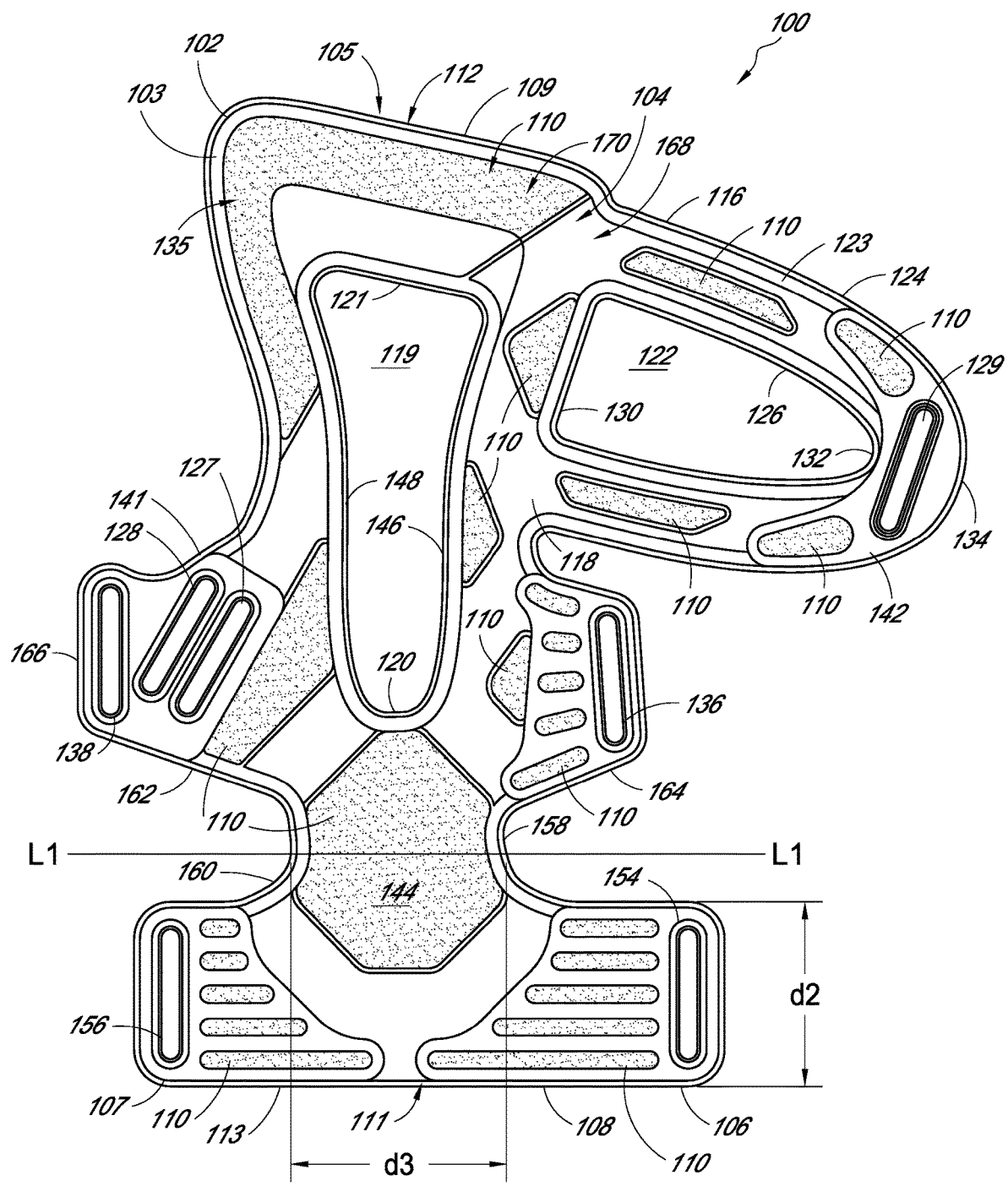
FIG. 1A is a plan view of an exterior side of an embodiment of an example of a carpal tunnel wrist ("CTW") brace 100 that when worn, is arranged on a portion of a user's palm, wrist and forearm, the illustrated exterior side being disposed facing away from (e.g., distal) to the user's palm. The brace 100 is illustrated as lying flat without straps to illustrate certain aspects of the brace 100. Typically, a forearm support 106 of the brace 100 is curvilinear in shape to generally align with the curve of the user's forearm, and a palm support 103 of the brace 100 is generally flat.

The following detailed description describes embodiments of carpal tunnel braces and methods, some of which are illustrated in the figures. These embodiments are not intended to be limiting, and various modifications, variations, combinations, etc., of the features of these embodiments are possible and within the scope of this disclosure.

Carpal tunnel syndrome is a condition that causes numbness, tingling and other symptoms in the hand and arm. Carpal tunnel syndrome is caused by pressure on the median nerve. The median nerve runs from your forearm through a passageway in your wrist (carpal tunnel) to your hand. It provides sensation to the palm side of your thumb and fingers, except the little finger. It also provides nerve signals to move the muscles around the base of your thumb (motor function). Anything that squeezes or irritates the median nerve in the carpal tunnel space may lead to carpal tunnel syndrome. Positions of extreme wrist flexion and extension are known to increase pressures within the carpal canal and apply pressure on the nerve. A wrist fracture can narrow the carpal tunnel and irritate the nerve, as can the swelling and inflammation resulting from rheumatoid arthritis.

The anatomy of your wrist, health problems and possibly repetitive hand motions can contribute to carpal tunnel syndrome. Carpal tunnel syndrome symptoms usually start gradually. The first symptoms often include numbness or tingling in your thumb, index and middle fingers that comes and goes. Carpal tunnel syndrome may also cause discomfort in your wrist and the palm of your hand. The surgical procedure performed for carpal tunnel syndrome is called a "carpal tunnel release." The surgical techniques relieve pressure on your median nerve by cutting the ligament that forms the roof of the tunnel. This increases the size of the tunnel and decreases pressure on the median nerve.

Although typically performed on an outpatient basis, recovery from carpal tunnel release surgery can be lengthy. Immediately following surgery, you will be encouraged to elevate your hand above your heart and move your fingers to reduce swelling and prevent stiffness. Pain, swelling, and stiffness after the procedure are common. Minor soreness in your palm may last for several weeks to several months. Grip and pinch strength usually return by about 2 to 3 months after surgery. If the condition of your median nerve was poor before surgery, however, grip and pinch strength may not improve for about 6 to 12 months. Common complications of carpal tunnel release surgery include bleeding, infection, and nerve aggravation or injury. Accordingly, it would be advantageous to be able to prevent or treat a carpal tunnel injury or inflammation to avoid the recovery time and risks of surgery.

To address treating carpal tunnel injury or inflammation, a carpal tunnel wrist brace can be designed to be support portions of the hand to mitigate carpal tunnel injury. In various embodiments, such a brace may be worn on a portion of a user's forearm, wrist, and palm, along the palm side of the user's hand. The brace may have a longitudinal axis that runs along a portion of the user's forearm, across the wrist, and across the proximal palmer to the distal palmer of a patient's hand.

The brace may include a forearm support that is aligned laterally to the longitudinal axis and is configured to support a portion of a patient's forearm. The form support may be curved to conform with the patient's forearm. A strap may be used to connect a first side of the forearm support to a second side of a forearm support to secure the form support to the patient's forearm. The brace may also include a wrist support that is generally aligned laterally to longitudinal axis of the brace. The wrist support is configured to support a portion of a patient's wrist to alleviate pressure on certain portions of the wrist which may aggravate carpal tunnel inflammation. The wrist support may be secured to the wrist by a strap that connects a first side of the wrist support to a second side of the wrist support across the top side of the wrist (i.e., referring to a portion the wrist that is on the same side as the back of the hand). The brace may also include a palmer support, arranged on the brace in a portion distal to the forearm support, to support the palmer portion of a patient's hand. In some embodiments, two members extend from the wrist support portion of the brace to the palmer support. The two members, the wrist support, and the palmer support define edges of a proximal palmer aperture in the brace.

The brace may also include a band that extends from the brace near the distal palmer support, and wraps across a portion of the back of the patient's hand when the brace is worn. A palmar strap coupled to the end of the band, may be used to secure the distal palmer support to the patient's hand. In some embodiments, the palmar strap attaches to a strap support on the side of the wrist support, passes over the purlicue of the hand and extends through a slot at the end of the band, and then connects to a fastening surface on the brace. The brace, been secured to a person's forearm wrist and hand by the forearm strap, wrist strap, and palmar strap, provides support to relieve pressure on the carpal tunnel in provides a secure rigid platform to keep a patient's hand in a preferred position for treatment and recovery of carpal tunnel.

ILLUSTRATIVE EMBODIMENT

An example of an embodiment of a brace is described below in reference to the figures. It will be appreciated by those of ordinary skill in the art that various modifications and changes may be made without departing from the scope of the described technology. Such modifications and changes are intended to fall within the scope of the embodiments. It will also be appreciated by those of ordinary skill in the art that parts included in one embodiment are interchangeable with other embodiments—one or more parts from a depicted embodiment can be included with other depicted embodiments in any combination. For example, any of the various components described herein and/or depicted in the figures may be combined, interchanged or excluded from other embodiments.

Below is a list of examples of certain components that are illustrated in examples included in certain figures of this disclosure, and that may be referenced in various embodiments of carpal tunnel wrist braces. In some instances, different terminology can be used for these components, for example, for clarity or brevity of description.

100 brace
    102 body
    103 palmar support
    104 distal exterior surface
    105 proximal exterior surface
    106 first forearm strap support
    107 second forearm strap support
    108 forearm support
    109 distal edge of the distal palmer support
    110 cutout in distal exterior layer
    111 first end of brace
    112 second end of brace
    113 proximal edge of the forearm support
    116 palmar band first connection
    118 palmar band second connection
    119 palmar aperture
    120 proximal end palmar aperture
    121 distal end palmar aperture
    122 palmar band aperture
    123 palmar band
    124 palmar band outside edge
    126 palmar band inside edge
    127 first palmar strap slot
    128 second palmar strap slot
    129 third palmar strap slot
    130 proximal end palm band aperture
    132 distal end palm band aperture
    134 distal end palmar band
    135 palmar strap fastening surface
    136 first wrist strap slot
    138 second wrist strap slot
    141 first palmar strap support
    142 second palmar strap support
    144 neck
    146 first longitudinal member
    148 second longitudinal member
    154 first forearm strap slot
    156 second forearm strap slot
    158 neck first edge
    160 neck second edge 162 wrist support
164 first wrist strap support
166 second wrist strap support
168 distal exterior layer
170 fastener layer
172 structure
174 proximal exterior layer
180 forearm strap
181 strap stop button
182 wrist strap
184 palmar strap
186 forearm
188 wrist
190 hand
192 fastener
194 proximal end of the structure 172
196 distal end of structure 172
198 distal end forearm strap
200 distal end palmar strap
202 distal end wrist strap FIG. 1A is a plan view of an exterior side of an embodiment of an example of a carpal tunnel wrist ("CTW") brace 100 that when worn, is arranged on a portion of a user's palm, wrist and forearm, the illustrated exterior surface 104 being disposed facing away from (e.g., distal) to the user's palm, and a proximal exterior surface 105 (FIG. 3) facing the patient's palm. The body 102 of the brace 100 is illustrated as lying flat, or substantially flat, and without straps (e.g., the forearm strap, the palmar strap, the wrist strap) to illustrate certain aspects of the brace 100. Typically, a forearm support 108 of the brace 100 is curvilinear in shape to generally align with the curve of the user's forearm, and a palmer support 103 of the brace 100 is generally relatively flat. For example, the brace 100 illustrated in FIGS. 3-6 and 8-14 shows an example of the curvilinear shape of a brace 100. For example, the curve of the forearm support 108 around a portion of a forearm, the curve of a wrist support 162 around a portion of a wrist, and the shape of the palmar support 103 along the palm of a hand. In some embodiments, the brace 100 includes a conformable rigid or semi-rigid structure 172 (FIG. 3) that allows a portion of the brace 100 to be deformed so as to conform with a portion of person's forearm (e.g., the brace 100 may be deformed and once it is deformed it maintains the deformed shape). For example, the forearm support 108 may be deformed to have a wide u-shaped curve to conform with the underside of a person's forearm when the brace is worn.

The embodiment of brace 100 illustrated in FIG. 1A includes the forearm support 108, a wrist support 162, and the palmer support 103. The brace 100 extends in longitudinal direction from a proximal edge 113 of the forearm support 108 on a first end 111 of the brace 100, to a distal edge 109 of the palmer support 103 on a second end 112 of the brace. The wrist support 162 is connected to the forearm support 108 by a neck 144 having a neck first edge 158 disposed on one lateral on the opposite lateral side of the neck 144. The wrist support 162 is connected to the palmar support 103 by a first longitudinal member 146 and a second longitudinal member 148 that extend between the wrist support 162 and a distal palmar support 103.

Figure 4:
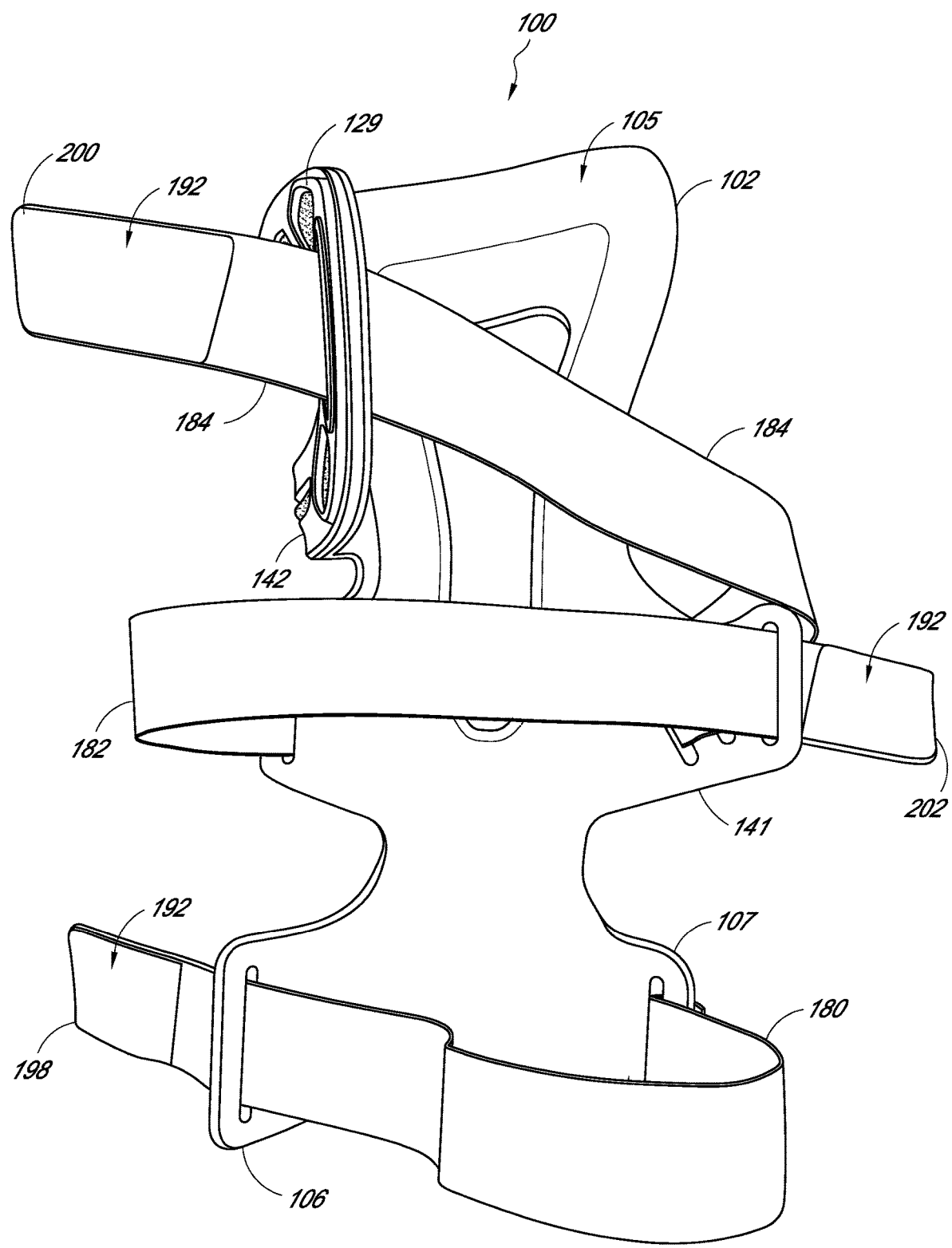
FIG. 4 is an illustration of the interior side of the brace of FIG. 3, shown with a forearm strap 180, a wrist strap 182, and a palmar strap 184 that are attached to the brace body 102 but not fastened in a configuration for securing the brace 100 to the user.

The forearm support 108 includes a first forearm strap support 106 disposed on a first lateral side of the forearm support 108 and a second forearm strap support 107 disposed on a second lateral side of the forearm support 108, the first lateral side of the forearm support 108 and the second forearm strap support 107 located on opposite lateral sides of the forearm support 108. The forearm strap supports 106, 107 are used to attached to a strap which secures the forearm support 108 to a patient's forearm. Although straps of the brace 100 are not shown in FIG. 1A, an example of a forearm strap 180, a wrist strap 182, and a palmar strap 184 are illustrated in FIG. 4. In addition, FIGS. 8-14 illustrate examples of the forearm strap 180, wrist strap 182, and palmar strap 184 being used to secure the brace 100 to a patient. In the illustrated embodiment, the first forearm strap support 106 includes a forearm strap first slot 154 and the second forearm strap support 107 includes forearm strap second slot 156. The forearm strap slots 154, 156 are elongated apertures in the brace 100, the elongation of the forearm strap slots 154, 156 generally aligned in the longitudinal direction of the brace 100. Also, the forearm strap supports 106, 107 can include a portion of the distal exterior layer 168 for strength. The distal exterior layer 168 may include rubber, or another durable natural or synthetic material.

The lateral sides of the neck 144 are narrower than the forearm support 108 and the wrist support 162. That is, the configuration of the neck 144 is such that the distance $d_3$ between the neck first edge 158 and the neck second edge 160 is less than the distance $d_1$ which is the lateral width of the forearm support 108, and the distance $d_3$ is less than the distance the distance $d_4$ which is the lateral width of the wrist support 162. The wrist support 162 and its corresponding wrist strap supports 164, 166 are configured such that at least a portion the wrist support 162 and its corresponding wrist strap supports 164, 166 deform as the wrist strap 182 is tightened (e.g., bend or flex to at least partially conform with the wrist of patient). In addition, in some embodiments (including the illustrated embodiment) the wrist support 162, although rigid, is at least somewhat deformable. For example, the wrist support 162 may be deformed and once it is deformed it maintains the deformed shape). Also, the forearm support 108 and its corresponding forearm strap supports 106, 107 are configured such that at least a portion the forearm support 108 and its corresponding forearm strap supports 106, 107 can deform as the forearm strap 180 is tightened.

In addition, in some embodiments (including the illustrated embodiment) the forearm support 108 although rigid can be deformable (e.g., it may be deformed and once it is deformed it maintains the deformed shape). The configuration and dimensions of the neck 144 allows the forearm support 108 and the wrist support 162 to be secured to a patient's forearm and hand independently, allowing each of the forearm support 108 and the wrist support 162 to independently conform to the forearm and wrist, respectively, as the forearm strap 180 and the wrist strap 182 are tightened to secure the brace 100 onto the patient. Also, the configuration and dimensions of the neck 144 allows the forearm support 108 and the wrist support 162 to be independently deformed as needed to fit a patient's arm and hand. In some embodiments, the forearm support 108 and the wrist support 162 may be deformed such they are not in the same plane, that is, the forearm support 108 and the wrist support 162 may me misaligned by (slightly) bending the brace at the neck 144. Accordingly and advantageously, the tightening the forearm strap 180 to secure the forearm support 108 to a patient with the proper fit, or deforming the forearm support 108 or the wrist support 162, will not affect the tightening of the wrist strap 182, or the deformation of the forearm support 108 or the wrist support 162 will not affect the deformation of the other of the forearm support 108 or the wrist support 162, to secure the wrist support 162 to the patient with the proper fit.

In the embodiment illustrated in FIG. 1A, the neck 144 includes a cutout 110 in the distal exterior layer 168 110. The brace 100, in the illustrated embodiment, includes a plurality of cutouts 110. A "cutout" as used herein in this context refers to an opening in the distal exterior layer 168 such that material that is disposed underneath the distal exterior layer 168 can be seen in the cutout 110. As described in more detail in reference to FIG. 7, the distal exterior layer 168 is an exposed distal exterior surface 104 of the brace 100, which is outward-facing, that is, it faces away from the palm of the patient when the brace is worn. In embodiments of the brace 100 that include multiple layers, a layer disposed adjacent to and underneath the distal exterior layer 168, which may normally not be exposed as it is covered by the distal exterior layer 168, may have a portion of such layer exposed through the one or more cutouts (openings) 110 in the distal exterior layer 168. In some embodiments, the material exposed through a cutout 110 is a material or structure that the strap can be fastened to. For example, by using corresponding hooks and loops fastening structures on the strap and on the layer exposed through a cutout, or using a snap, or any other suitable fastening structure.

Still referring to FIG. 1A, the wrist support 162 includes a first wrist strap support 164 positioned on one lateral side (e.g., a first side) of the wrist strap support 162, and a second wrist strap support 166 positioned on the opposite lateral side (e.g., a second side) of the wrist support 162. The first wrist strap support 164 includes a first wrist strap slot 136. In this embodiment, the elongation of the strap slot 136 is generally aligned in the longitudinal direction of the brace 100. The second wrist strap support 166 includes a second wrist strap slot 138. In this embodiment, the elongation of the strap slot 138 is generally aligned in the longitudinal direction of the brace 100. Wrist strap 182 (e.g., FIG. 8) can be attached to one of the wrist strap slots 136, 138, extend around the user's wrist through the other of the wrist strap slots 136, 138, and then be fastened to either the strap 182 or somewhere else on the brace.

The first longitudinal member 146 and the second longitudinal member 148 extend from the wrist support 162 towards and are attached to the distal palmar support 103. The wrist support 162, the first longitudinal member 146, the second longitudinal member 148, and the palmar support 103 define a proximal palmar aperture 119, which is structured to align with a portion of a patient's hand when the brace 100 is worn. In this embodiment, the proximal palmar aperture 119 includes a U-shaped proximal end 120 and a longer distal end 121 which in this embodiment includes a straight portion that runs along a portion of the palmar support 103. In other embodiments, the edges of the first longitudinal member 146, the second longitudinal member 148, the wrist support 162, and palmar support 103 may be different in length, curvature, and/or alignment, and correspondingly the shape of the proximal palmar aperture 119 may be different. The configuration of the palmar aperture 119 advantageously allows for airflow through the palmar aperture 119 across a patient's palm exposed palm (exposed by the palmar aperture 119) while still providing the rigid support of the wrist and hand as needed, which may mitigate sweating, and thus be more comfortable for a patient to wear for extended periods of time.

Still referring to FIG. 1A, the brace 100 includes a palmar band 123 extending from a lateral portion of the first longitudinal member 146. The palmar band 123 is attaches to an outside edge of the first longitudinal member 146 at a palmar band first connection 116 and a palmar band second connection 118 at a portion on the first longitudinal member 146 that is closer to the first end 111 of the brace. The palmar band 123 in this embodiment is generally U-shaped, although other configurations of the palmar band 123 that perform the same functionality are also contemplated. A palmar band aperture 122 extends from a proximal end 130 to a distal end 132 and is within the U-shaped structure of the palmar band 123, the palmar band aperture 122 been defined by the palmar band inside edge 126 which runs along the perimeter of the palm band aperture 122.

A first palmar strap support 141 is disposed on a portion of the wrist support 162 in the illustrated embodiment of FIG. 1A, the first palmar strap support 141 disposed between the second wrist strap support 166 and the centerline (or longitudinal axis) of the brace 100 that runs from the first end 111 to the second end 112. The first palmar strap support 141 includes a first palmar strap slot 127, and a second palmar strap slot 128 adjacently disposed by the first palmar strap slot 127 and parallel in alignment to the first palmar strap slot 127. The palmar band 123 includes a distal end 134 and the second palmar strap support 142 is located on the distal end 134. The second palmar strap support 142 includes a third palmar strap slot 129. The proximal end of a palmar strap 184 (FIG. 4) may be attached to the first Palmar strap support 141. When the brace 100 is worn, the palmar strap 184 may run across a portion of the purlicue of the patient's hand. A distal end of the palmar strap 184 may pass through the third palmar strap slot 129 when the palmar band 123 is across the back of the hand, across a portion of the purlicue of the hand, and then the distal end of the palmar strap may attach to the brace 100, for example, on the palmar strap fastening surface 135. In this embodiment, the palmar strap passing surface 135 is part of the fastener layer 170 that is exposed in a cutout 110 of the distal exterior layer 168. An illustration of the palmar strap 184 securing the brace 100 to a patient's hand is illustrated and described in more detail in FIGS. 8-14.

Figure 1B:
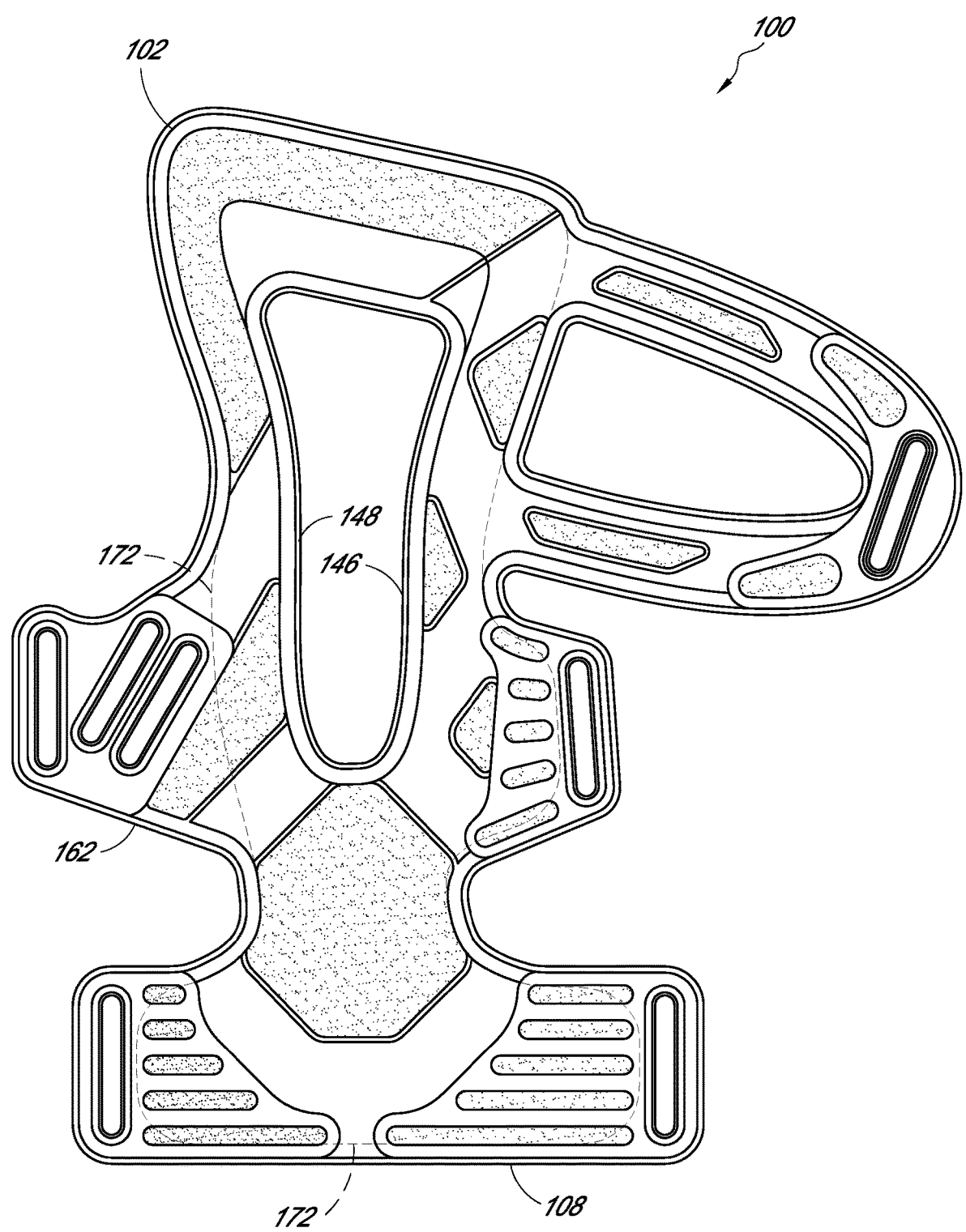
FIG. 1B is a plan view of the brace 100 illustrated in FIG. 1A but also showing a semi-rigid internal structure 172 which is included in a portion of the forearm support 106, the wrist support 162, the first and second longitudinal members 148, 150, and the lateral palmar support 103.

FIG. 1B is a plan view of the brace 100 illustrated in FIG. 1A showing an example of a structure 172 provides rigidity to portions of the brace 100. Portions of the structure 172 are included in the forearm support 108, the wrist support 162, the first and second longitudinal members 146, 148, and the palm support 103. That is, the illustrated structure 172 extends from the forearm support 108, through the neck 44 to the wrist support 162. Portions of the structure 172 further extend through the first and second longitudinal member 146, 148, and then to the palmar support 103. The structure 172 surrounds the palmar aperture 119 (FIG. 1) to provide rigidity to the brace 100 as a whole to limit (separate) movement of a person's forearm, wrist, and hand.

Figure 1C:
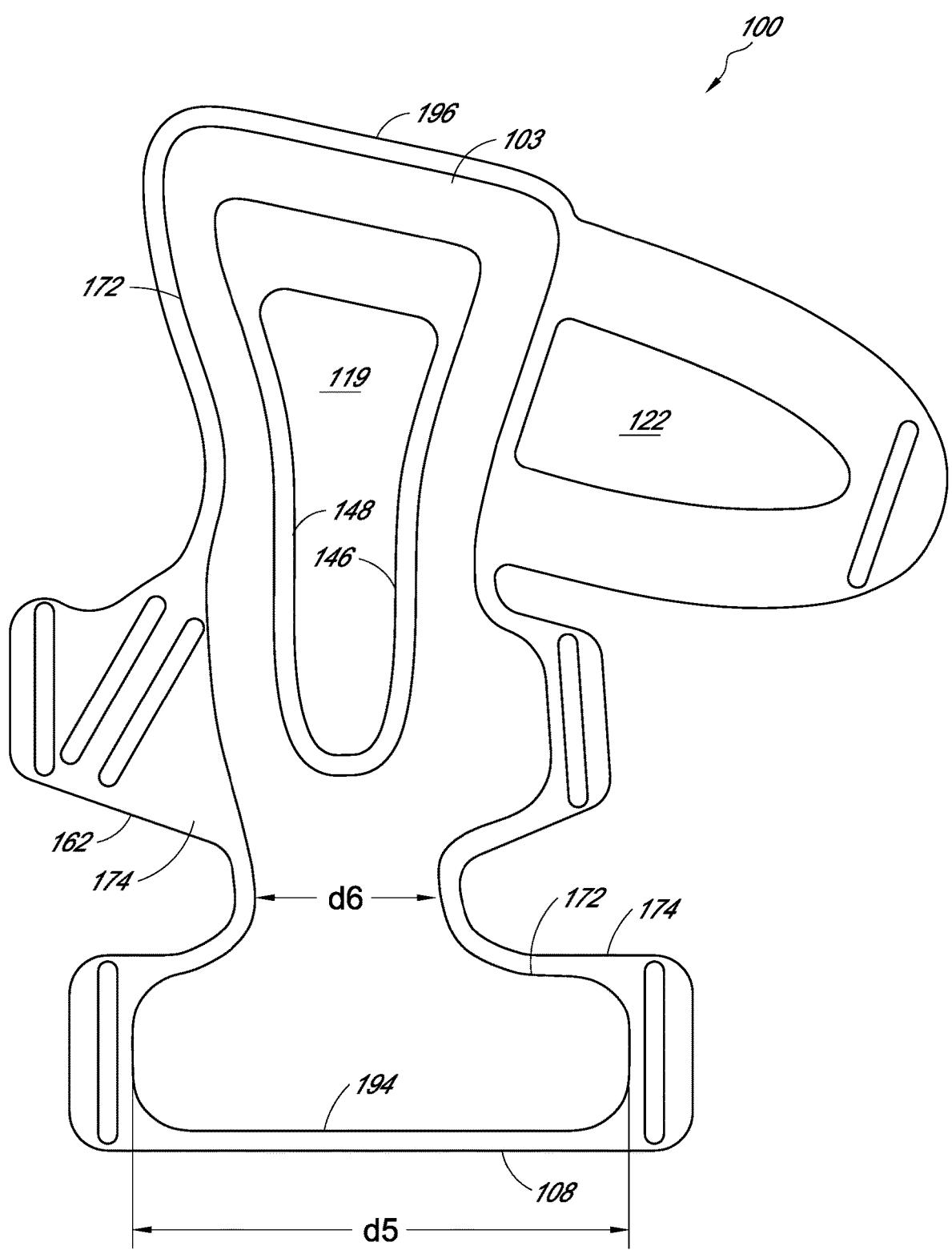
FIG. 1C is a plan view of a portion of the brace 100 illustrated in FIG. 1A, showing the semi-rigid internal structure 172 without the rubber first layer 168 and the fabric second layer 170 (that is, the rubber first layer 168 and the fabric second layer 170 have been removed in this illustration).

FIG. 1C is a plan view of a portion of the brace 100 illustrated in FIG. 1A, showing the structure 172 without the rubber first layer 168 and the fabric second layer 170 (that is, the rubber first layer 168 and the fabric second layer 170 are not shown in this illustration). As described above, the components of brace 100 are shown as being flat, however, as used in worn by a patient, one or more of the forearm support 108, wrist support 162, the first and second longitudinal members 146, 148, and the palmar support 103 may be at least slightly curved (or deformed) to conform to the patient's forearm, wrist, and hand. The structure 172 may comprise a rigid, or a semi-rigid (rigid but deformable) material. In some embodiments, the structure can be deformed to a shape to better fit the brace 100 to the patient's arm/hand, and after it is deformed it is rigid and maintains the deformed shape. In some embodiments where there are many different sizes of the brace 100, the structure 172 may not be deformable and one of the many sizes of the brace 100 are selected for a particular application on a patient. In various embodiments, the structure 172 may comprise metal, plastic, a composite material, wood, fiberglass, or another suitable material. In some embodiments, structure 172 comprises titanium, steel, aluminum, or an alloy.

In the embodiment illustrated in FIG. 1C, the structure 172 is arranged on the brace 100 from a proximal end 194 in the forearm support 108 through the neck 44, and continues through a portion of the wrist support 162 and extends in each of the longitudinal members 146, 148 to the distal palmar support 103, and laterally across distal palmar support 103 to a distal end 196 of the structure 172. Similar to the forearm support 108, the structure 172 extends laterally such that a lateral dimension $d_5$ of the structure 172 in the form support 108 portion of the brace is greater than a lateral dimension $d_6$ of the structure 172 in the neck 44 region of the brace. Portions of structure 172 in the wrist support 162, the longitudinal members 146, 148, in the distal palmar support 103 surround the proximal palmar aperture 119. In some embodiments, structure 172 may be formed by two or more structural members that are rigidly coupled together, loosely coupled, or not joined (except indirectly through another structure).

Figure 2:
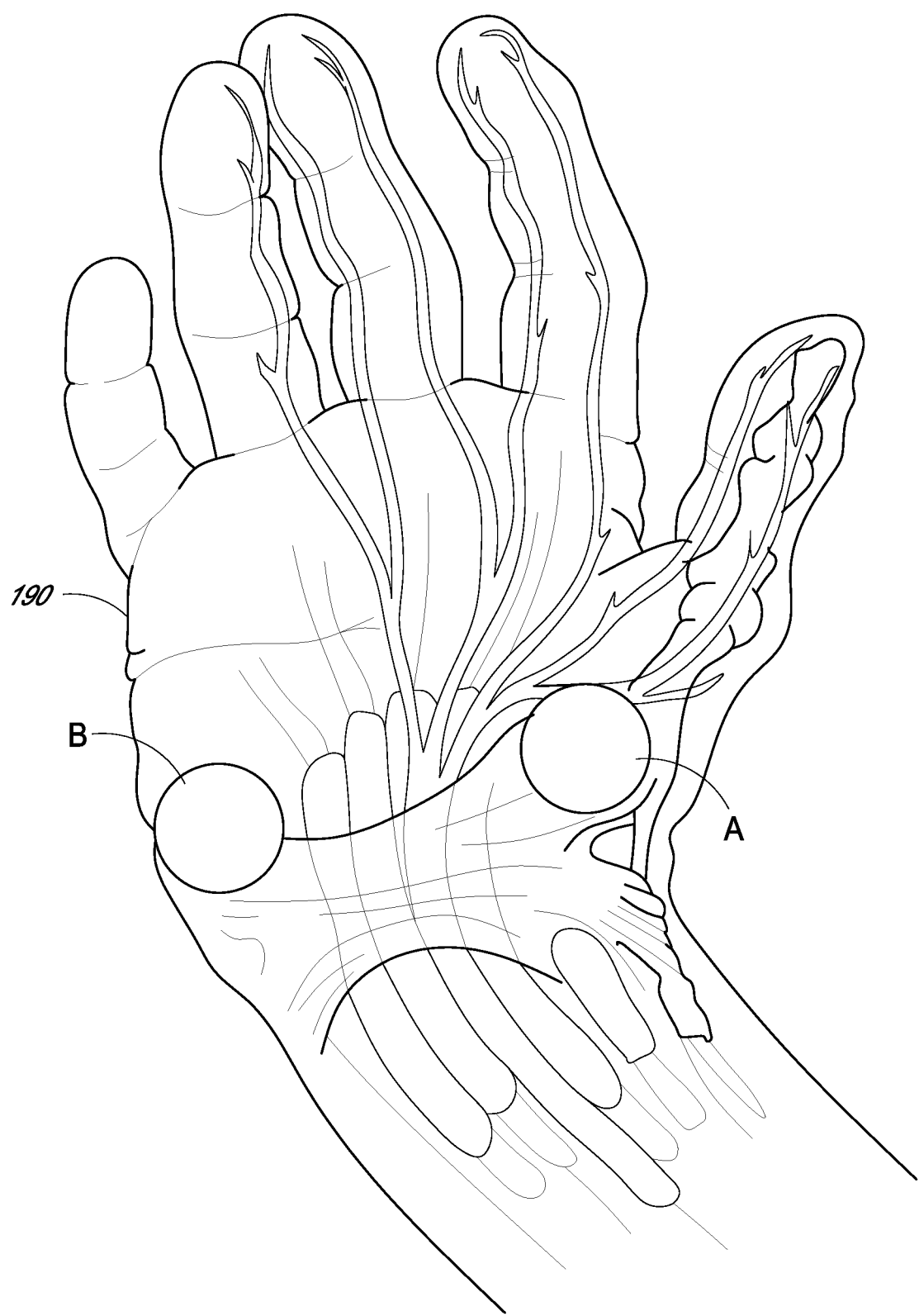
FIG. 2 is an illustration of a hand showing two portions of the hand that the CTW brace 100 is structured to support, the brace applying pressure at these two portions to release pressure on the carpal tunnel portion of the hand/wrist.

FIG. 2 is an illustration showing two portions of a hand 190 of a patient that the brace 100 is structured to support. When worn by a patient, the brace 100 supports portions A and B of the hand 190, applying pressure at these two portions when the hand 190 is resting on the surface, with the brace 100 between the hand in the surface, to release pressure on the carpal tunnel portion of the hand and/or wrist.

Figure 3:
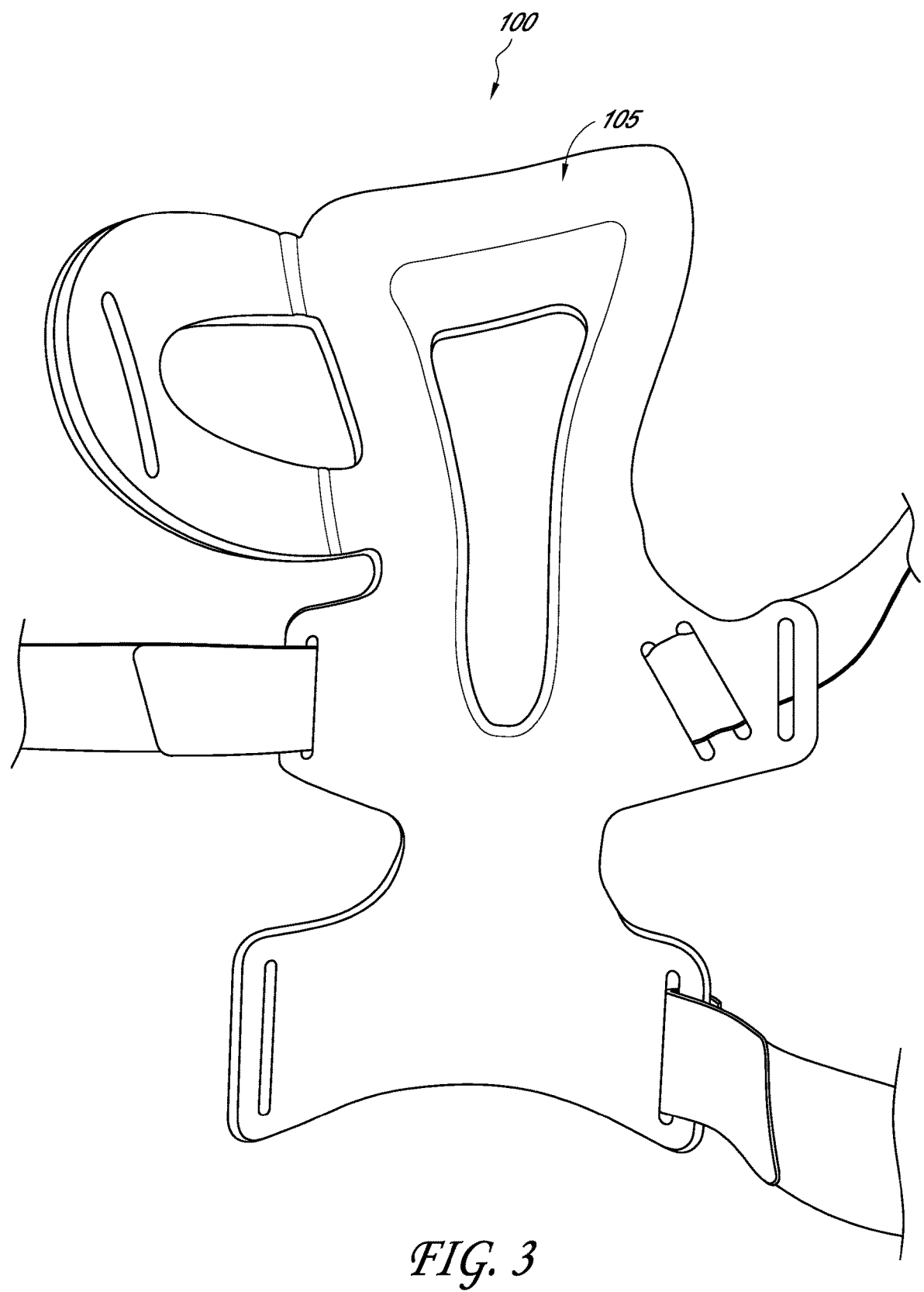
FIG. 3 is an illustration of the interior side of the brace of FIG. 1A without straps.

FIG. 3 is an illustration of the proximate exterior surface 105 of the embodiment of the CTW brace 100 of FIG. 1, shown here with straps, which are described in more detail hereinbelow. The proximate exterior surface 105 is the surface of the brace 100 that is adjacent to, and contacts, the patient's forearm wrist and hand when the brace is worn. The proximate exterior surface 105 may comprise a material that is comfortable to be worn against the skin. For example the proximate exterior surface 105 may comprise a natural or synthetic fabric, or other material, that has good durability and is comfortable to be worn against the patient's skin for an extended period of time. As described in reference to FIG. 7, the proximate exterior surface 105 may be the surface of the proximate exterior layer 174. In some embodiments, the proximate exterior layer 174 may comprise a padded material, a hypoallergenic material, a soft material, a smooth material, and/or a material that is not irritating.

FIG. 4 is an illustration of the proximate exterior surface 105 (the interior side) of the brace of FIG. 1, shown with a forearm strap 180, a wrist strap 182, and a palmar strap 184 that are attached to the brace body 102 but not fastened in a configuration for securing the brace 100 to the patient. In FIG. 4, the forearm strap 180 is shown as being attached to one of the forearm strap supports 106, 107 and having a distal end 198 of the forearm strap 180 extending through the forearm strap slot in the other of the forearm strap supports 106, 107. The wrist strap 182 is shown as being attached to one of the wrist strap supports 164, 166 and having a distal end 202 of the wrist strap 182 extending through the wrist strap slot in the other of the wrist strap supports 164, 166. The palmar strap 184 is shown as being attached to the first palmar strap support 141 and having a distal end 200 extending through the third palmar strap slot 129 in the palmar strap second support 142. The distal end of each of the forearm strap 180, the wrist strap 182, and the palmar strap 184 includes a fastener 192 that may be used to removably attach the distal end of the strap to a portion of the brace 100 or to the strap itself.

Figure 5:
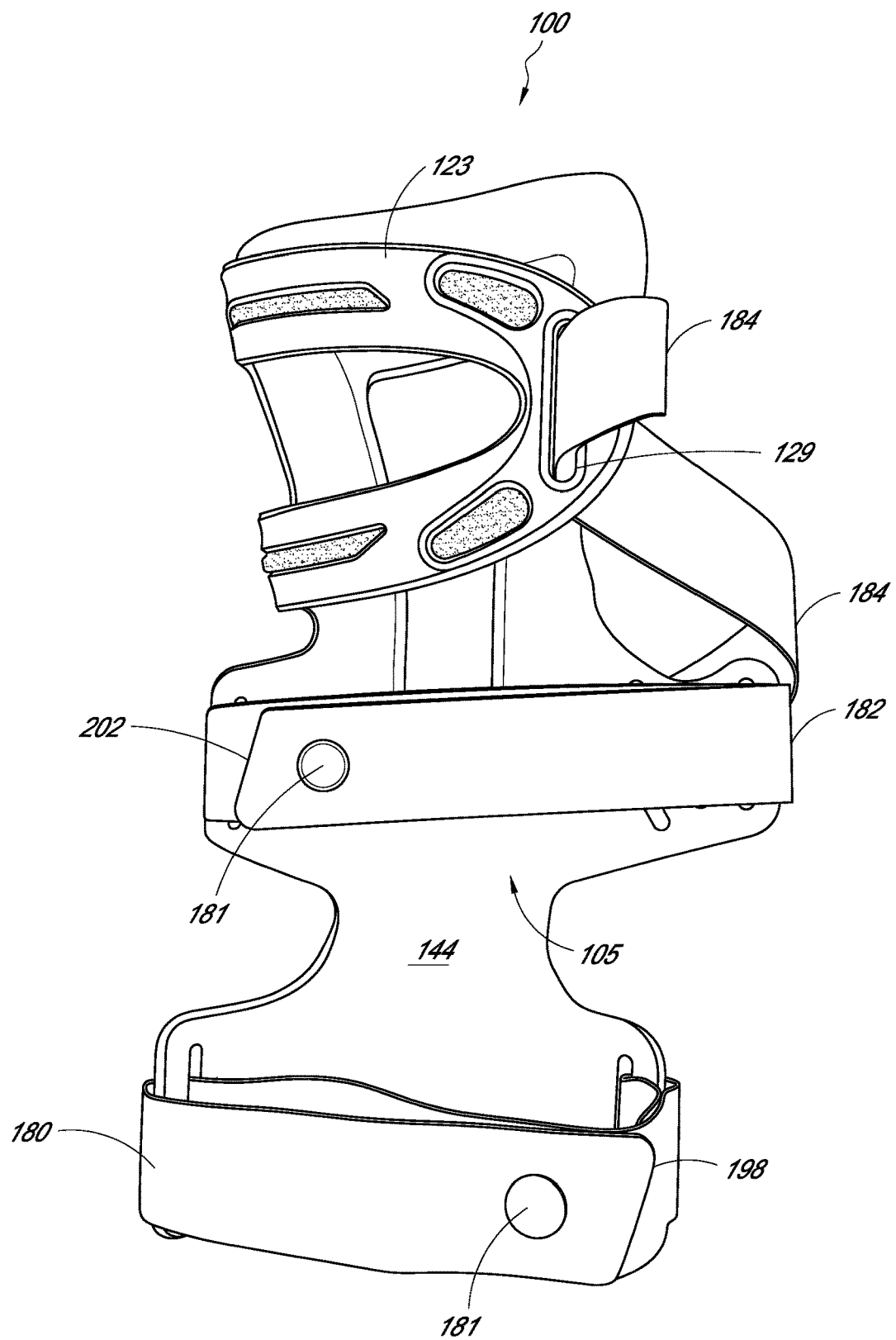
FIG. 5 is an illustration of the interior side of the brace of FIG. 3, shown with a forearm strap 180, a wrist strap 182, and a palmar strap 184 that are attached to the brace body 102 and in a configuration for securing the brace 100 to the user.

FIG. 5 is an illustration of the interior side of the CTW brace of FIG. 3, shown with a forearm strap 180, a wrist strap 182, and a palm strap 184 that are attached to the brace body 102 and in a configuration for securing the brace 100 to the user. In the illustrated configuration, the distal end 198 of the forearm strap 180 is doubled-back and attached to the forearm strap 180, and the distal end 202 of the wrist strap 182 is doubled-back and attached to a portion of the wrist strap 182. The palmar strap 184 passes through the third palmar strap slot 129 and loops back around to the other side of the brace 100, and can attach to palmar strap fastening surface 135 (FIG. 1).

Figure 6:
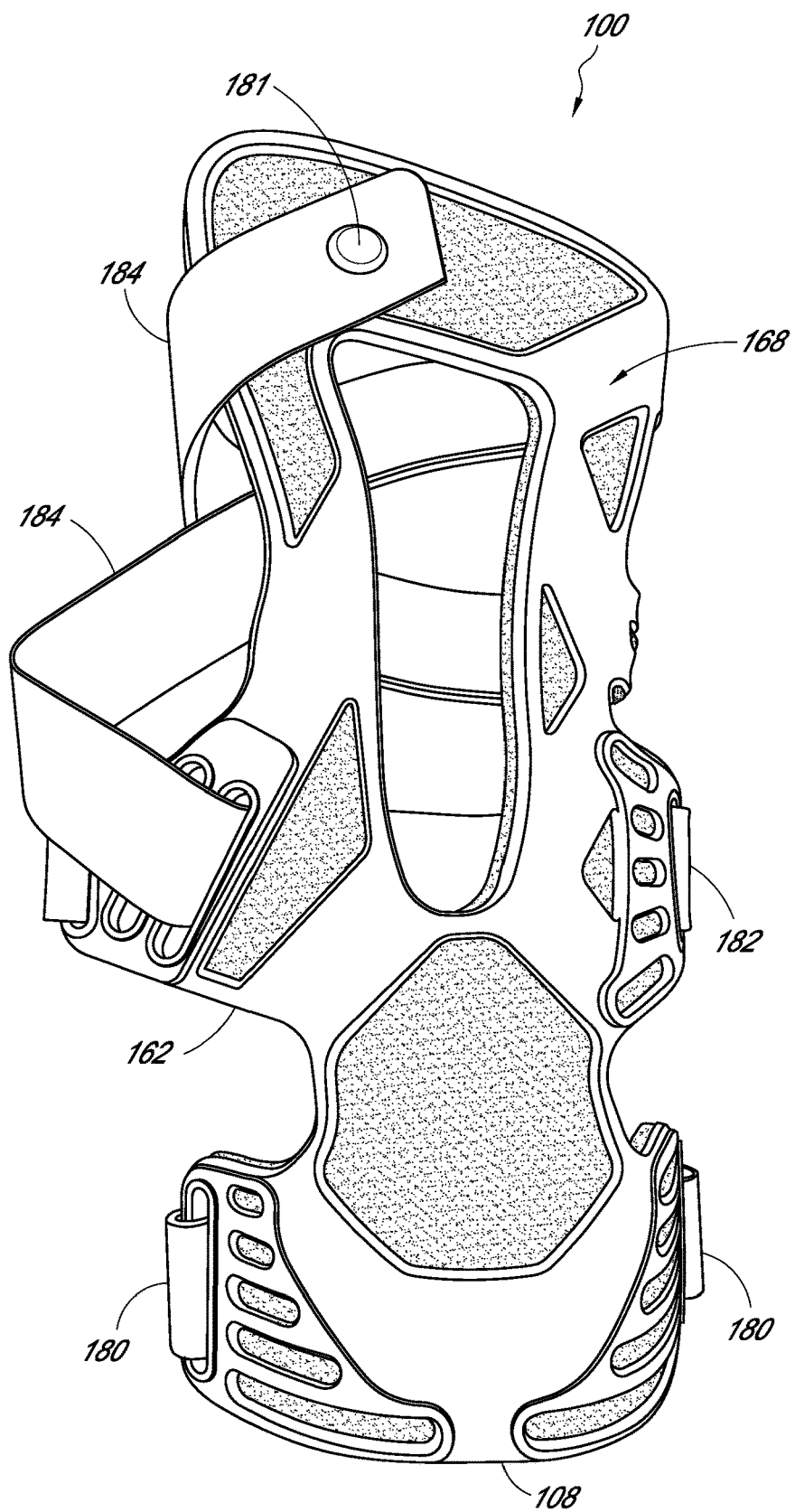
FIG. 6 is an illustration of the exterior side of the brace of FIG. 3, shown with a forearm strap 180, a wrist strap 182, and a palmar strap 184 that are attached to the brace body 102 and in a configuration for securing the brace 100 to the user.

As illustrated in the embodiments in FIG. 5 and FIG. 6, the brace 100 may include a strap stop button 181 disposed near the distal end of the forearm strap 180 and/or the wrist strap 182 (FIG. 5), and/or the palmar strap 184 (FIG. 6). The strap stop button 181 is a structure that is attached to a strap and has a depth dimension that is slightly larger than the width of a strap slot of the brace 100 that the strap passes through, preventing the end of the strap from passing through the slot at an undesirable time, for example, when preparing to put the brace 100 on. In some embodiments, the stop strap button 181 is a metal structure that couples to a portion of the strap. For example, a strap stop button 181 attached near the distal end 198 of the forearm strap 180 increases a depth dimension of the strap where the stop strap button 181 is disposed such that the combination of the stop strap button 181 and the strap is slightly larger than the width of the forearm strap slots 154, 156. A strap stop button 181 attached near the distal end 202 of the wrist strap 182 has a depth dimension that the combination of the stop strap button 181 and the wrist strap 182 is slightly larger than the width of the wrist strap slots 136, 138. A strap stop button 181 attached near the distal end 200 of the palmar strap 184 has a depth dimension such that the combination of the stop strap button 181 and the palmer strap 184 is slightly larger than the width of the palmar strap slot 129. In some embodiments, the strap stop button 181 may be just larger than the width of the slot such that with some force the distal end of the strap including the strap stop button can pass through the slot (as the material of the slot can be pliable), but such that it is unlikely to occur unless desired. A stop strap button 181 may be attached to one side of a strap during manufacture of the strap such that one side of the stop strap button protrudes from the outside of the strap (that is, on the opposite side as the fastener 192) and the other side of the stop strap button 181 is covered by a portion of the strap (e.g., the fastener 192) such that it is not exposed.

FIG. 6 is an illustration of the brace 100 showing the distal exterior surface 104. The brace 200 is shown with the forearm strap 180, the wrist strap 182, and the palmar strap 184 that are attached to the brace body 102 and in a configuration for securing the brace 100 to the hand of a patient.

FIG. 7 is a cross-sectional view schematic representing an example of layers of the brace 100 of FIG. 1A along line $L_1$-$L_1$, according to some embodiments. In this example, the layers of the brace include a distal exterior layer 168, a fastener layer 170, a semi-rigid structure layer 172, and a proximal exterior layer 174. The distal exterior layer 168 may comprise a durable and flexible material, for example, rubber or any suitable natural or synthetic material. When the brace 100 is attached to the patient's hand, the distal exterior layer 168 is disposed facing away from the patient's hand, wrist, and forearm. The distal exterior layer 168 may include a number of cutouts 110 (FIG. 1) that allow the fastener layer 170 to be exposed through the distal exterior layer 168. In some embodiment, the cutouts 110 also may facilitate increased flexibility of the in the areas of the cutouts 110. In some embodiments, the cutouts 110 form part of the ornamental design of the brace 100.

The fastener layer 170 is disposed adjacent to the distal layer 168, between the distal exterior layer 168 and the proximal exterior layer 174. In this embodiment, the faster layer 170 is also disposed adjacent to the semi-rigid structure 172 such that the faster layer 170 is between the distal exterior layer 168 and the semi-rigid structure 172 in the portions of the brace that include the semi-rigid structure 172. The fastening layer 170 may provide a fastening surface that a portion of any of the straps of the brace may be attached to, according to various embodiments. For example, the fastening layer 170 may comprise hooks or loops, a corresponding surface of a strap may comprise the other of the hooks or loops.

In this embodiment, the semi-rigid structure 172 is disposed adjacent to, and between, the fastening layer 170 and the proximal exterior layer 174. The semi-rigid structure 172 provides rigidity to the brace 100 in the portions of the brace 100 that include the semi-rigid structure 172. The proximal exterior layer 174, when the brace is worn on a patient's hand, is adjacent to the patient's hand in context the patient's hand. The proximal exterior layer 174 may comprise any suitable synthetic or natural fabric. In some embodiments the proximal exterior layer 174 is hypoallergenic. In some embodiments the proximal exterior layer 174 comprises a material which is non-absorptive to make it easier to clean.

FIGS. 8-14 are illustrations of different stages of the brace 100 of FIG. 1A been attached to a patient by the forearm strap 180, the wrist strap 182, and the palm strap 184. Some of the components described may refer to components of the brace 100 shown in FIG. 1A.

Figure 8:
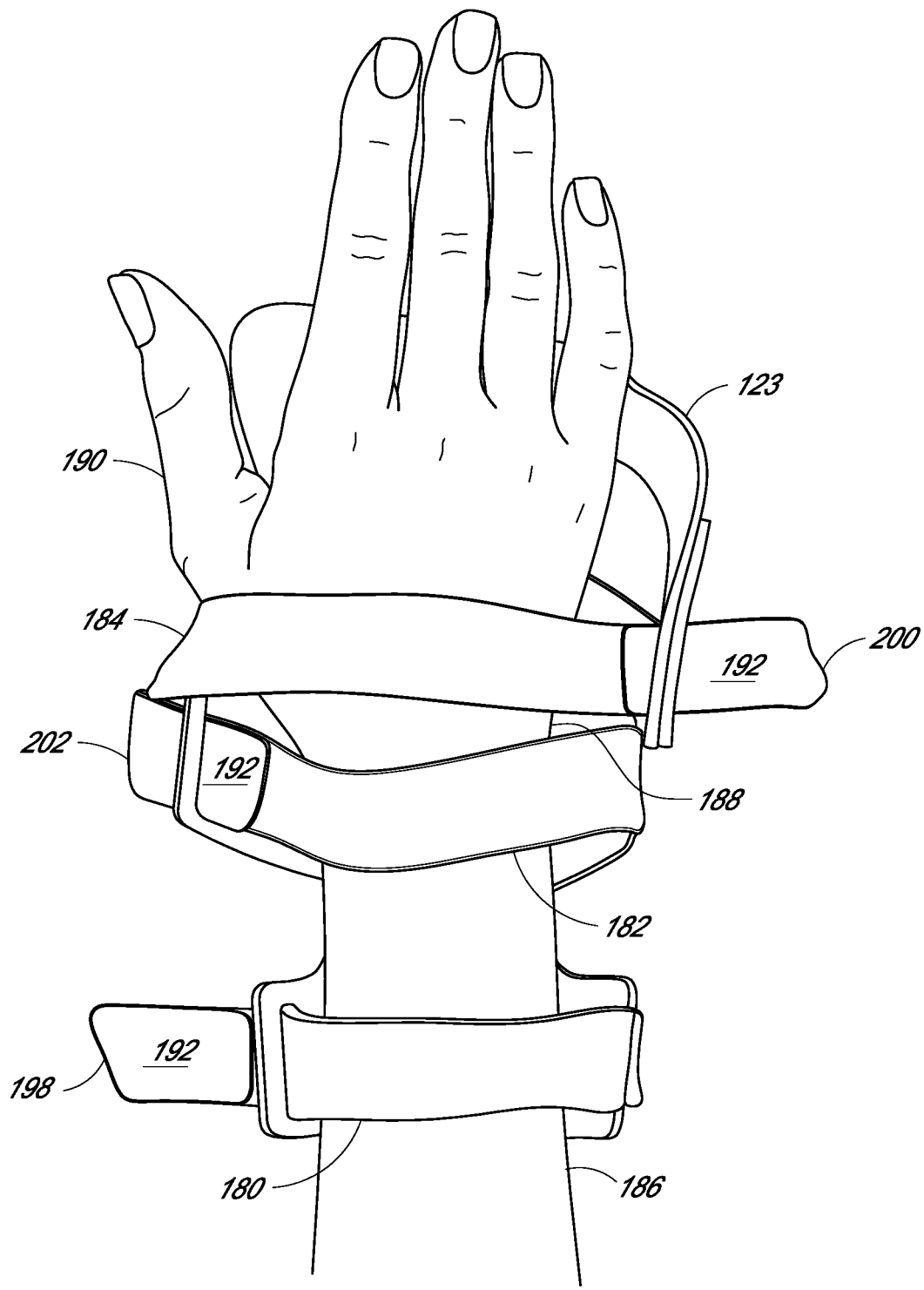
FIG. 8 is an illustration of the brace of FIG. 1A being secured on the forearm, wrist and hand of a patient, showing straps of the brace across a portion of the topside of the forearm, wrist and hand.

FIG. 8 is an illustration of a CTW brace on the topside of a hand 190 of a user before the straps are secured. As is illustrated in FIG. 8, the forearm strap 180 is attached to a forearm support 108 at the forearm strap first support 106 and extends across the top of the forearm 186 and through the forearm strap second slot 156. The forearm strap 180 includes a fastener 192 that may be attached to another portion of the brace 100 to secure the forearm strap 180, and the forearm support 108, to the patient's forearm 186. In some embodiments, the portion of the brace 100 that the brace fastener 192 attaches to is the forearm strap 180. In some embodiments, the portion brace 100 that the brace fastener 192 attaches to is a surface on the body 102 of the brace 100.

The wrist strap 182 is shown attached to one side of the wrist support 162 and passes across the top of the wrist 188 to the opposite side of the wrist support 162 where it passes through the second wrist strap support 166. The wrist strap 182 includes a fastener 192 that may be attached to another portion of the brace 100 to secure the wrist strap 182, and the wrist support 162, to the patient's wrist 188. In some embodiments, the portion of the brace 100 that the fastener 192 attaches to is the wrist strap 182. In some embodiments, the portion of the brace 100 that the fastener 192 attaches to is a surface on the body 102 of the brace 100.

The palmar strap 184 is shown attached to the first palmar strap support 141, running across the back of the hand 190, and passing through the third palmar strap slot 129. The palmar strap 184 includes a fastener 192, on the distal end of the palmar strap 184, that may be attached to another portion of the brace 100 to secure the palmar strap 184 and the distal palmar support 103 to the patient. In some embodiments, the portion of the brace 100 that the fastener 192 attaches to is a surface on the body 102 of the brace 100, for example, the palmar strap fastening surface 135. In other embodiments, the fastener 192 of the palmar strap 24 may be attached to another part of the brace 100 that has a suitable fastening surface, e.g., a surface of the brace or a strap of the brace.

Figure 9:
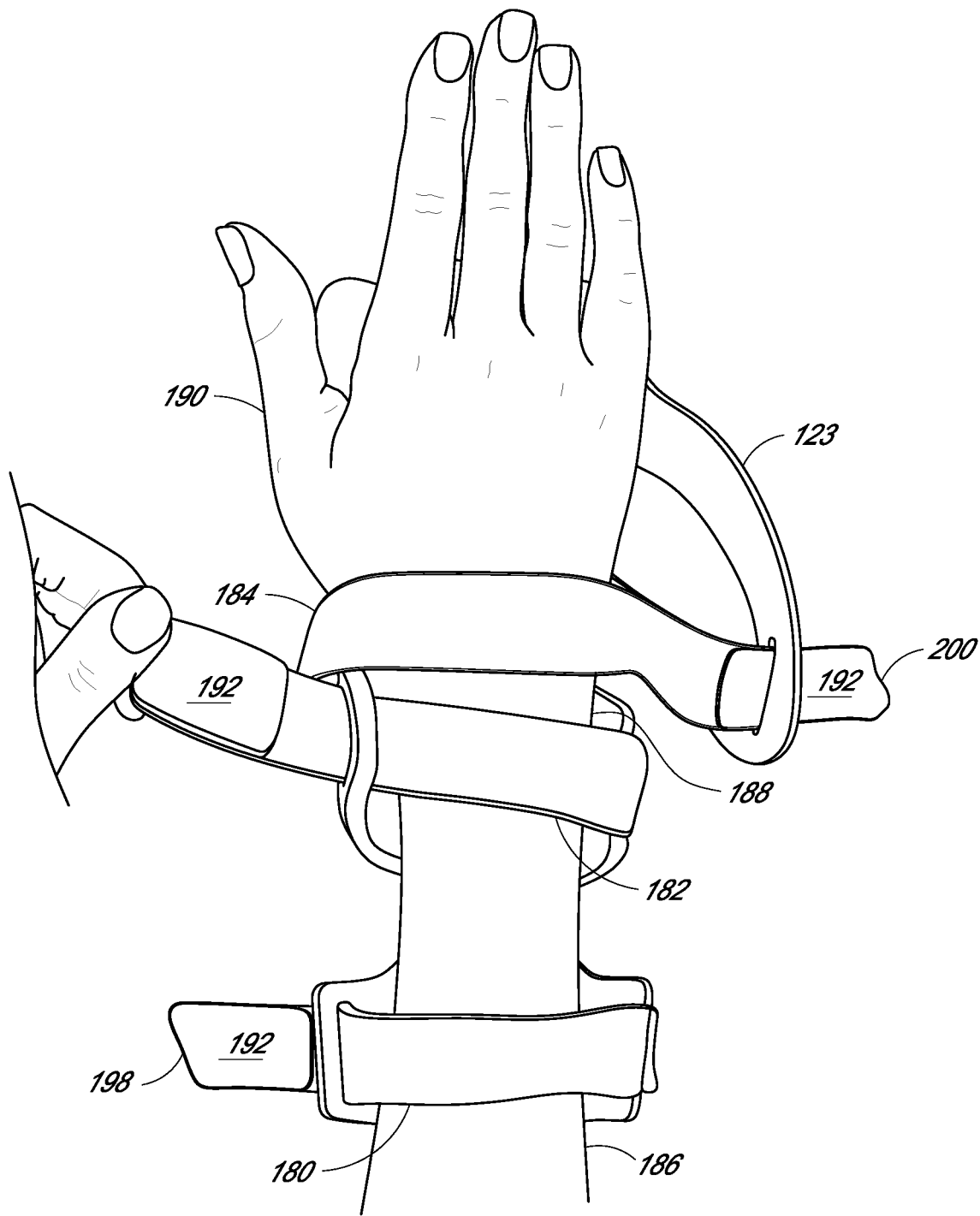
FIG. 9 is another illustration of the brace of FIG. 1A being secured on the forearm, wrist and hand of a patient, showing straps of the brace across a portion of the topside of the forearm, wrist and hand.

FIG. 9 is another illustration of the brace of FIG. 1A being secured on the forearm, wrist and hand of a patient, showing straps of the brace across a portion of the topside of the forearm 186, wrist 188, and hand 190 of a patient. In FIG. 9, the forearm strap 180 is illustrated in a unfastened position, that is, the distal end 198 of the forearm strap 180 is not been doubled back onto the forearm strap 180 such that the fastener 192 on the distal end 198 fastens to a portion of the forearm strap 180. Similarly, the wrist strap 182 is illustrated in unfastened positioned, that is, the fastener 192 on the wrist strap 182 is not yet been doubled back onto the wrist strap 182 to fasten the wrist strap 182 onto the wrist 188. The palmar strap 184 is shown as extending across the topside of hand 190 through the palmar strap slot 129 of the palm band 123, that is, the distal end 200 of the palmar strap 184 is extending through the palmar strap slot 129.

Figure 10:
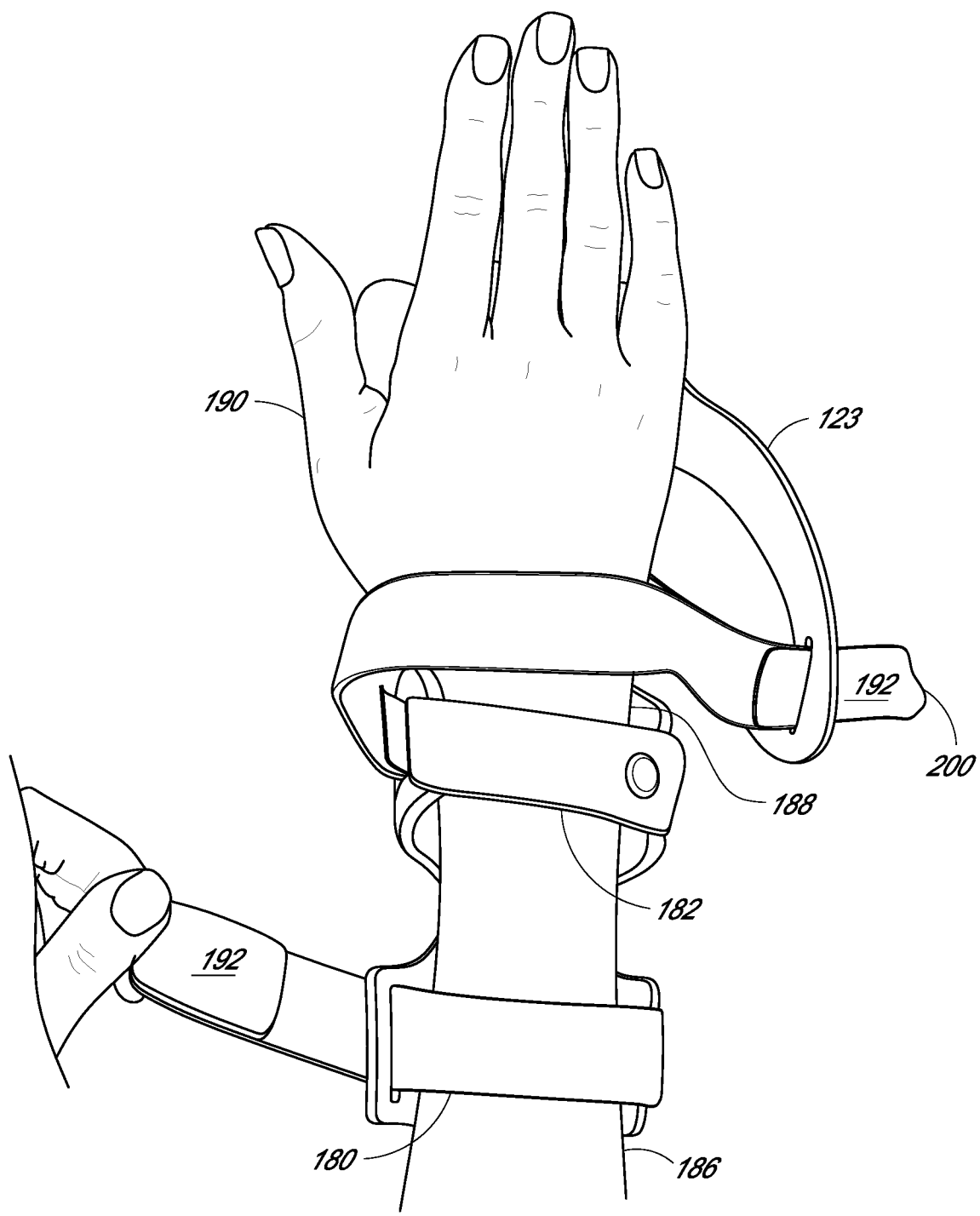
FIG. 10 is another illustration of the brace of FIG. 1A being secured on the forearm, wrist and hand of a patient, showing straps of the brace across a portion of the topside of the forearm, wrist and hand.

FIG. 10 is another illustration of the brace of FIG. 1A being secured on the forearm 186, wrist 188, and hand 190 of a patient, showing straps 180, 182, 184 of the brace across a portion of the topside of the forearm 186, wrist 188, and hand 190. In FIG. 10, the wrist strap 182 has been secured across the patient's wrist 188. Forearm strap 180 is shown being tightened on the patient's forearm 186.

Figure 11:
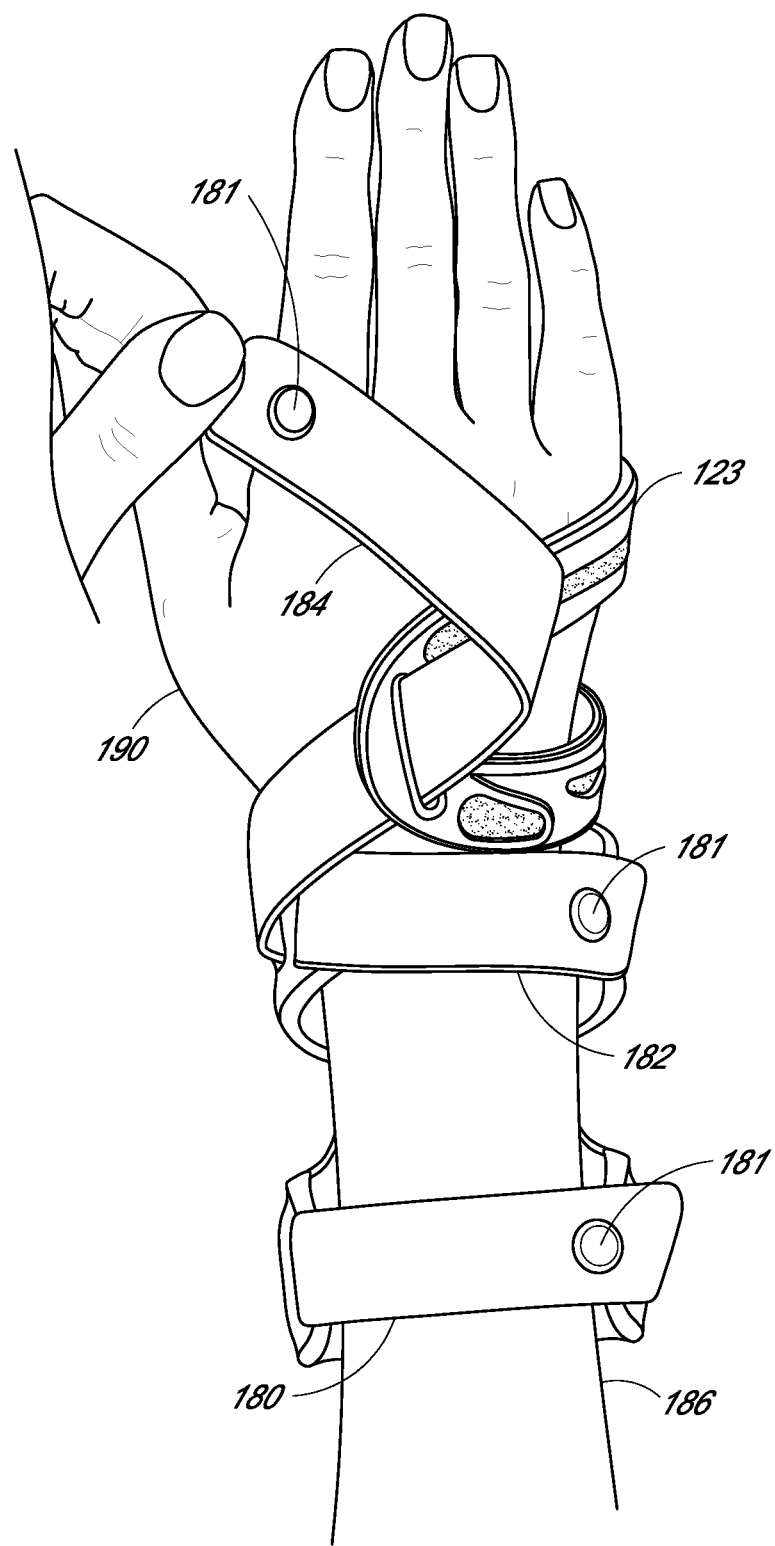
FIG. 11 is another illustration of the brace of FIG. 1A being secured on the forearm, wrist and hand of a patient, showing straps of the brace across a portion of the topside of the forearm, wrist and hand, with the forearm strap and the wrist strap secured.

FIG. 11 is another illustration of the brace of FIG. 1A being secured on the forearm 186, wrist 188, and hand 190 of a patient, showing straps of the brace across a portion of the topside of the forearm 186, wrist 188, and hand 190. In FIG. 11, the forearm strap 180 and the wrist strap 182 is secured. The palm band 123 is shown as extending across a portion of the topside of the hand 190. The palmar strap 184, extending through the palm strap 123, is being pulled across another portion of the topside of the hand 190 such that it will extend across a portion of the hand between the thumb and the fingers of the patient, so that it can be secured to a portion of the brace, as illustrated in FIG. 12.

Figure 12:
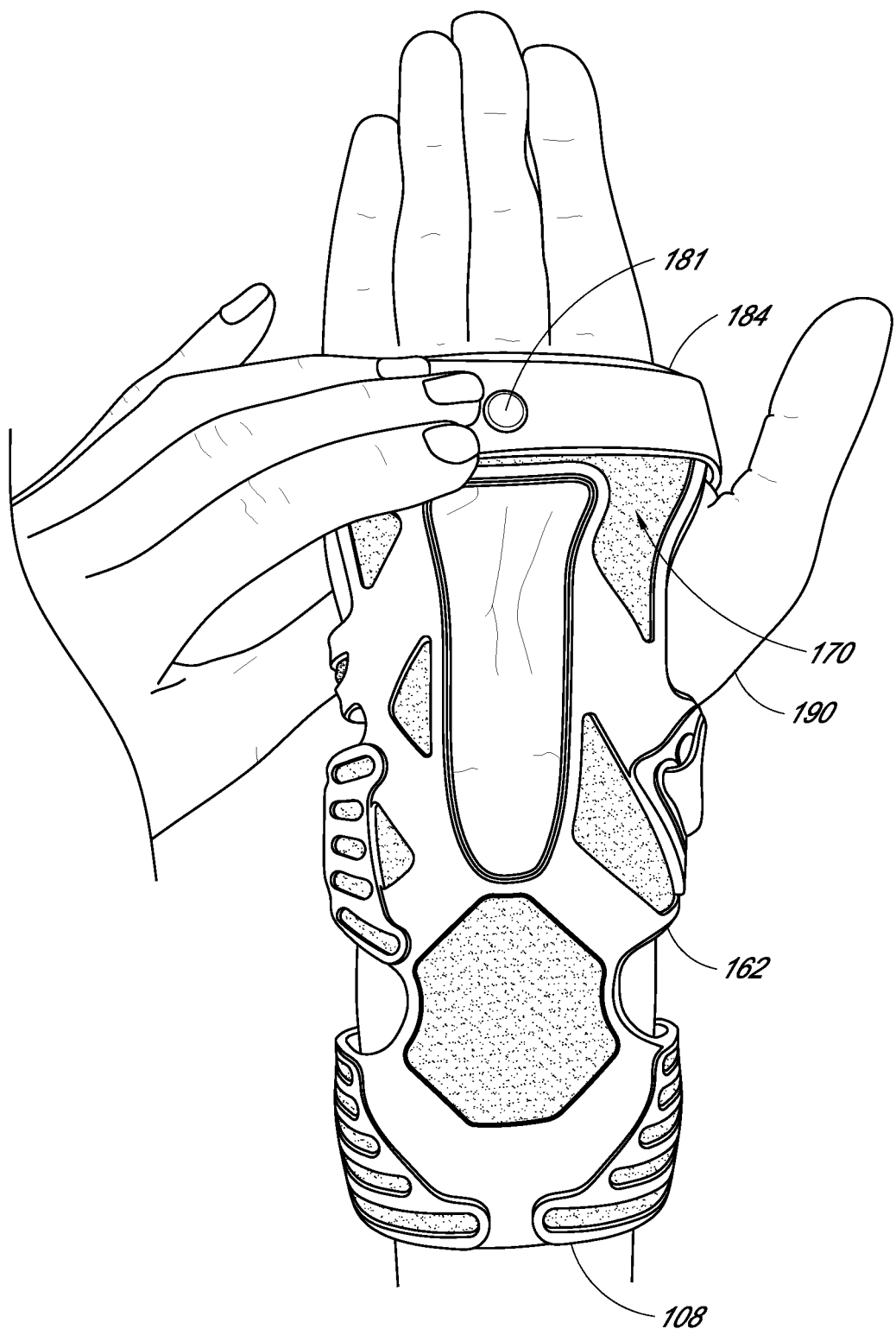
FIG. 12 is another illustration of the brace of FIG. 1A being secured on the forearm, wrist and hand of a patient, showing the brace on the palm-side of the hand and the palmar strap being secured.

FIG. 12 is another illustration of an embodiment of a brace of the type illustrated in FIG. 1A being secured on the forearm, wrist and hand of a patient, showing the brace on the palm-side of the hand 190 and the palmar strap 184 being secured to a portion of the brace. The fastener 192 on the distal end 200 of palmar strap 184 is secured to a portion of a fastening layer 170 which, in various embodiments, may extend across various portions of the distal exterior surface 104 (FIG. 1A). This allows the palmar strap 184 to be secured such that it holds the brace securely to the patient's hand for various size and shapes of the hand.

Figure 13:
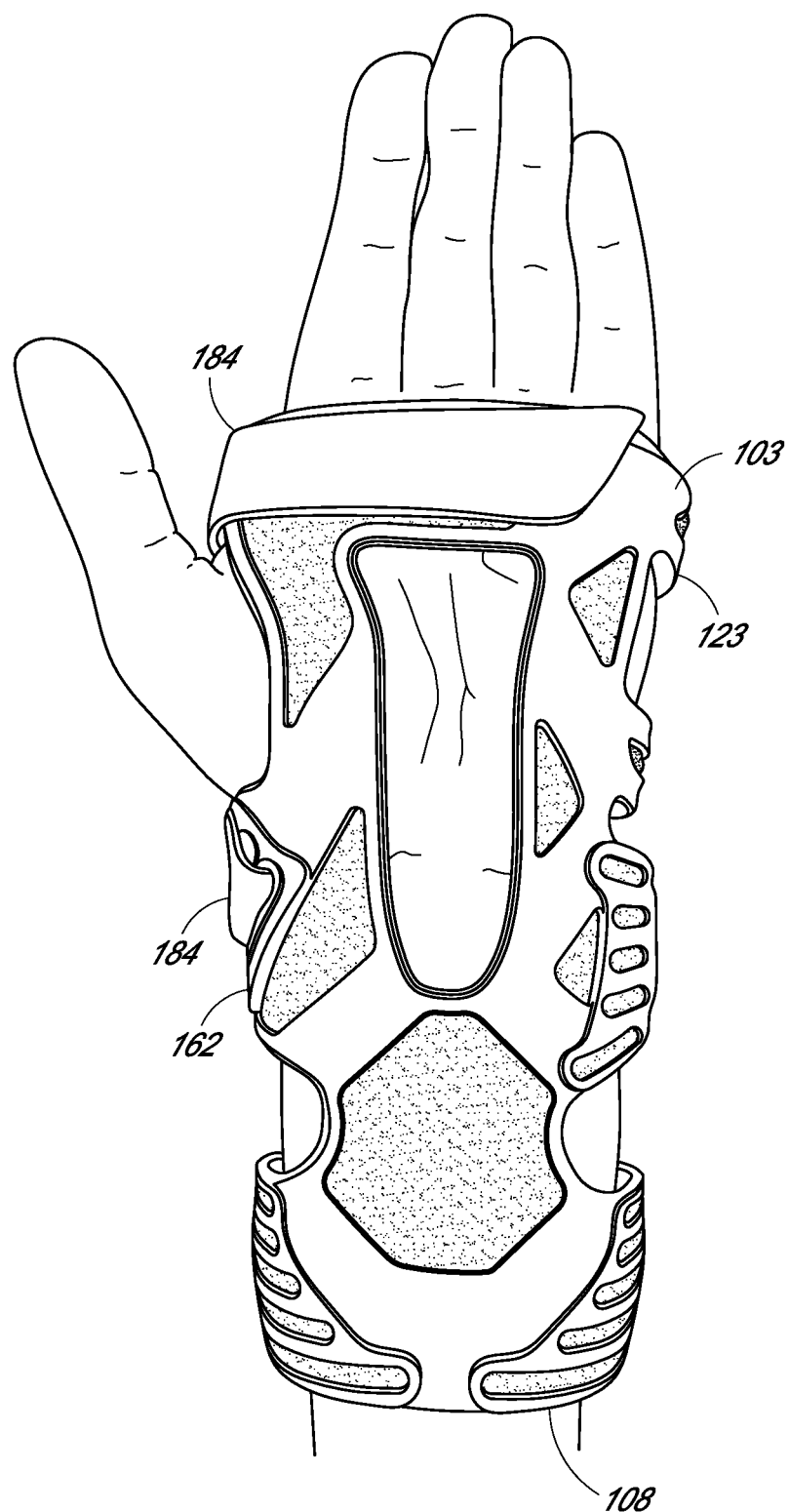
FIG. 13 is another illustration of the brace of FIG. 1A being secured on the forearm, wrist and hand of a patient, showing the brace on the palm-side of the hand and the palmar strap secured.

FIG. 13 is another illustration of an embodiment of a carpal tunnel brace on the left hand of a patient. FIG. 13 also illustrates the palmar strap 184 being fastened to a fastening surface of the brace that is on the palmer support 103.

Figure 14:
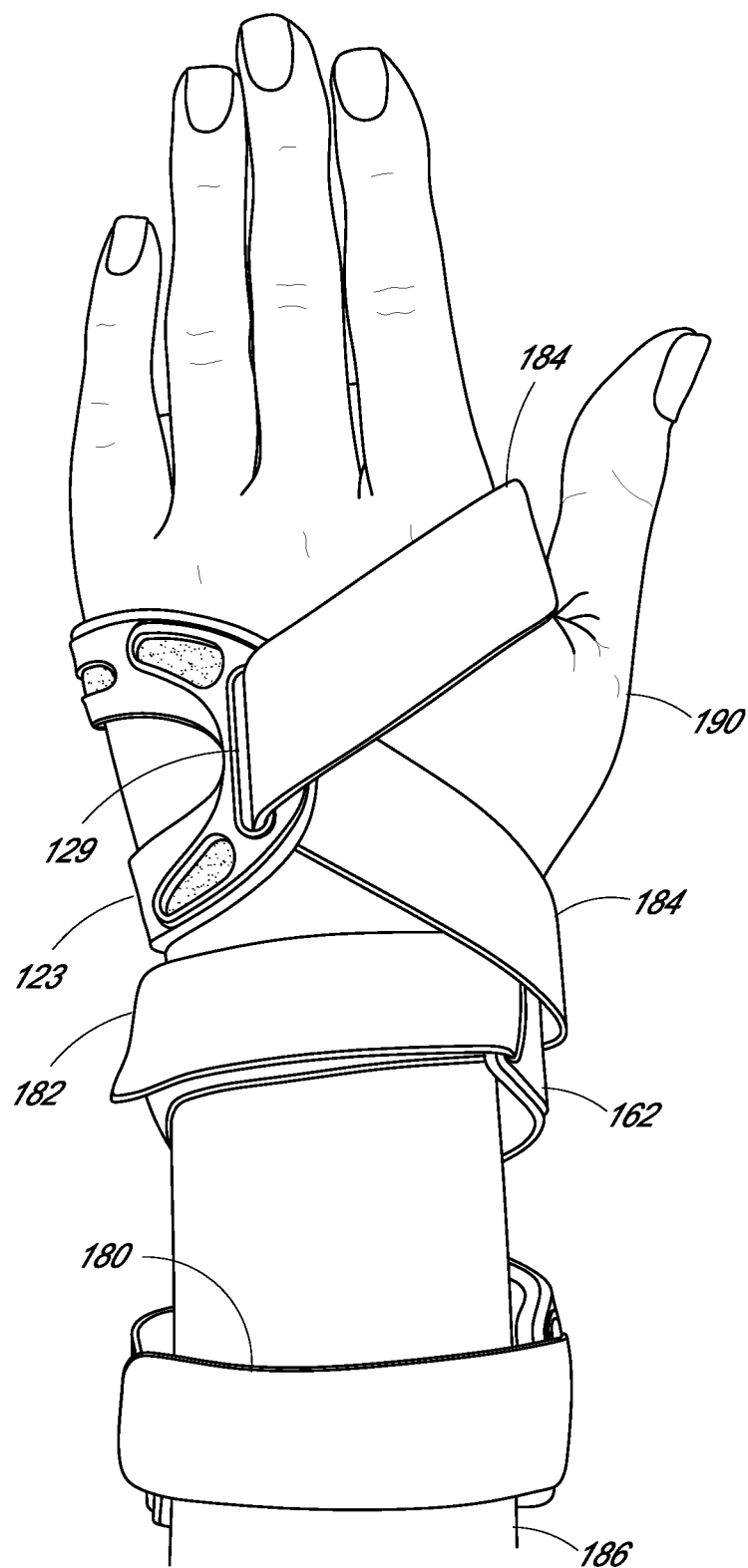
FIG. 14 is an illustration of a brace on the top-side of a hand with the brace secured on the forearm, wrist and hand.

FIG. 14 is an illustration of a brace on the top-side of a hand with the brace secured on the forearm 186, wrist 188, and hand 190 of a patient further illustrating the configuration of the forearm strap 180, the wrist strap 182, and the palmar strap 184 in a fully secured position. That is, the wrist strap 182 is secured to a portion of itself. The forearm strap 180 is secured to a portion of itself. In the palmar strap 184 is secured to the fastening surface 170 (shown in FIGS. 1A and 12) on the other side of the brace.

EXAMPLES OF EMBODIMENTS

Example 1

A brace for carpal tunnel injury, including a body having a proximal end and a distal end defining a longitudinal direction, the body including a forearm support at the body proximal end; a wrist support coupled to the forearm support by a neck portion, the wrist support including a first palmar strap support disposed on a lateral side of the wrist support; a first member and a second member extending from the wrist support in the longitudinal direction towards the distal end; a distal palmar support coupled to the wrist support by the first and second member; a proximal palmar aperture surrounded by the wrist support, the first and second members and the palm support, the proximal palmar aperture configured to fit over a portion of the proximal palmer of a hand; a palm band coupled to the first member at a proximal end and extending laterally from the first member to a distal end, the palm band comprising a second palmar strap support at the palm band distal end, the palm band configured to extend from the first member across a portion of the back of the hand when the brace is worn; and a palmar strap extending between a proximal end, attached to the first palmar strap support, to a distal end, the palmer strap configured to extend through the second palmer strap support across a portion of the back of the hand and over a purlicue of the hand, the distal end of the palmar strap configured to removably attach to the distal palmar support.

Example 2

The brace of example 1, further including a first wrist strap support and a second wrist strap support arranged on opposite lateral sides of the wrist support; and a wrist strap having a proximal end attached to the first wrist strap support, a distal end of the wrist strap configured to extend through the second wrist strap support and removably attach to a portion of the brace to secure the wrist support to a hand when the brace is worn.

Example 3

The brace of example 2, where the distal end of the wrist strap is configured to removably attach to the wrist strap.

Example 4

The brace of any of examples 1-3, wherein the first palmer strap support comprises an elongated first and second slot, and the proximal end of the palmar strap passing through the first and second slot to attach the palmer strap to the first palmar support.

Example 5

The brace of any of example 1, further including a first wrist strap support on a lateral side of the wrist support, the first wrist strap support having an elongated slot configured to receive a wrist strap, wherein the first palmer strap support is aligned on the same lateral side of the wrist support as the first wrist strap support, the first palmer strap support including an elongated first and second slot aligned in parallel, and wherein the elongated slot of the first wrist strap support is aligned at an angle with the first and second slots of the first palmar strap support such that the elongated slot of the first wrist strap support is not aligned parallel to the first and second slots of the first palmar strap support.

Example 6

The brace of example 5, wherein the elongated slot of the first wrist strap support is disposed distal to the longitudinal axis of the brace relative to the first and second slots of the first palmar strap support.

Example 7

The brace of any one of examples 1-6, further including a first forearm strap support and a second forearm strap support arranged on opposite lateral sides of the forearm support; and a forearm strap having a proximal end attached to the first forearm strap support, a distal end of the forearm strap configured to extend through the second forearm strap support and removably attach to a portion of the brace to secure the forearm support to a forearm when the brace is worn.

Example 8

The brace of example 7, wherein the distal end of the forearm strap is configured to removably attach to the forearm strap.

Example 9

The brace of example 7, wherein the distal end of the forearm strap is configured to removably attach to a fastening surface on the brace.

Example 10

The brace of example 9, wherein the fastening surface is a fabric.

Example 11

The brace of any one of examples 1-10, wherein the brace further comprises a distal exterior layer on the surface of the brace facing away from the hand when the brace is worn.

Example 12

The brace of example 11, wherein the first layer is rubber.

Example 13

The brace of any one of examples 1-12, wherein the brace further comprises a proximal exterior layer on the surface of the brace facing towards the hand when the brace is worn.

Example 14

The brace of examples 13, wherein the proximal exterior layer is a fabric.

Example 15

The brace of any one of examples 1-14, further comprising a semi-rigid layer disposed between the distal exterior layer and the proximal exterior layer.

Example 16

The brace of any example 15, wherein the semi-rigid layer comprises metal.

Example 17

The brace of claim 15, wherein the semi-rigid layer comprises plastic.

Example 18

The brace of claim 15, wherein the semi-rigid layer comprises a composite material.

Example 19

The brace of any one of examples 1-18, further comprising a fastener layer disposed between the distal exterior layer and the semi-rigid layer, wherein the distal exterior layer includes at least one cutout that exposes a portion of the fastener layer.

Example 20

The brace of claim 19, wherein the fastener layer is configured such that a portion of at least one strap of the brace may removably attach to a portion of the fastener layer exposed in a cutout of the distal exterior layer.

The foregoing description details certain embodiments of the systems, devices, and methods disclosed herein. It will be appreciated, however, that no matter how detailed the foregoing appears in text, the systems, devices, and methods can be practiced in many ways. As is also stated above, it should be noted that the use of particular terminology when describing certain features or aspects of the invention should not be taken to imply that the terminology is being re-defined herein to be restricted to including any specific characteristics of the features or aspects of the technology with which that terminology is associated.

Conditional language such as, among others, "can," "could," "might" or "may," unless specifically stated otherwise, are otherwise understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Headings are included herein for reference and to aid in locating various sections. These headings are not intended to limit the scope of the concepts described with respect thereto. Such concepts may have applicability throughout the entire specification.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

The phrase "based on" does not mean "based only on," unless expressly specified otherwise. In other words, the phrase "based on" describes both "based only on" and "based at least on." Unless otherwise explicitly stated, articles such as "a" or "an" should generally be interpreted to include one or more described items. Accordingly, phrases such as "a device configured to" are intended to include one or more recited devices.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims. Applicant reserves the right to submit claims directed to combinations and sub-combinations of the disclosed inventions that are believed to be novel and non-obvious. Inventions embodied in other combinations and sub-combinations of features, functions, elements and/or properties may be claimed through amendment of those claims or presentation of new claims in the present application or in a related application. Such amended or new claims, whether they are directed to the same invention or a different invention and whether they are different, broader, narrower or equal in scope to the original claims, are to be considered within the subject matter of the inventions described herein.

What is claimed is:

1. A brace for carpal tunnel injury, comprising:
    a body having a proximal end and a distal end defining a longitudinal direction, the body including
        a forearm support at the body proximal end;
        a wrist support coupled to the forearm support by a neck portion, the wrist support comprising a first palmar strap support disposed on a lateral side of the wrist support;
        a first member and a second member extending from the wrist support in the longitudinal direction towards the distal end;
        a distal palmar support coupled to the wrist support by the first and second member;
        a proximal palmar aperture surrounded by the wrist support, the first and second members and the palmar support, the proximal palmar aperture configured to fit over a portion of the proximal palm of a hand;
        a palm band coupled to the first member at a proximal end and extending laterally from the first member to a distal end, the palm band comprising a second palmar strap support at the palm band distal end, the palm band configured to extend from the first member across a portion of the back of the hand when the brace is worn; and
    a palmar strap extending between a proximal end, attached to the first palmar strap support, to a distal end, the palmar strap configured to extend through the second palmar strap support across a portion of the back of the hand and over a purlicue of the hand, the distal end of the palmar strap configured to removably attach to the distal palmar support.

2. The brace of claim 1, further comprising:
    a first wrist strap support and a second wrist strap support arranged on opposite lateral sides of the wrist support; and
    a wrist strap having a proximal end attached to the first wrist strap support, a distal end of the wrist strap configured to extend through the second wrist strap support and removably attach to a portion of the brace to secure the wrist support to a hand when the brace is worn.

3. The brace of claim 2, wherein the distal end of the wrist strap is configured to removably attach to the wrist strap.

4. The brace of claim 1, wherein the first palmar strap support comprises an elongated first and second slot, and the proximal end of the palmar strap passing through the first and second slot to attach the palmar strap to the first palmar support.

5. The brace of claim 1, further comprising
a first wrist strap support on a lateral side of the wrist support, the first wrist strap support having an elongated slot configured to receive a wrist strap,
wherein the first palmar strap support is aligned on the same lateral side of the wrist support as the first wrist strap support, the first palmar strap support including an elongated first and second slot aligned in parallel, and
wherein the elongated slot of the first wrist strap support is aligned at an angle with the first and second slots of the first palmar strap support such that the elongated slot of the first wrist strap support is not aligned parallel to the first and second slots of the first palmar strap support.

6. The brace of claim 5, wherein the elongated slot of the first wrist strap support is disposed distal to the longitudinal axis of the brace relative to the first and second slots of the first palmar strap support.

7. The brace of claim 1, further comprising:
a first forearm strap support and a second forearm strap support arranged on opposite lateral sides of the forearm support; and
a forearm strap having a proximal end attached to the first forearm strap support, a distal end of the forearm strap configured to extend through the second forearm strap support and removably attach to a portion of the brace to secure the forearm support to a forearm when the brace is worn.

8. The brace of claim 7, wherein the distal end of the forearm strap is configured to removably attach to the forearm strap.

9. The brace of claim 7, wherein the distal end of the forearm strap removably attaches to a fastening surface on the brace.

10. The brace of claim 9, wherein the fastening surface is a fabric.

11. The brace of claim 10, wherein the brace further comprises a distal exterior layer on the surface of the brace facing away from the hand when the brace is worn.

12. The brace of claim 11, wherein the distal exterior layer is rubber.

13. The brace of claim 11, wherein the brace further comprises a proximal exterior layer on the surface of the brace facing towards the hand when the brace is worn.

14. The brace of claim 13, wherein the proximal exterior layer is a fabric.

15. The brace of claim 13, further comprising a semi-rigid layer disposed between the distal exterior layer and the proximal exterior layer.

16. The brace of claim 15, wherein the semi-rigid layer comprises metal.

17. The brace of claim 15, wherein the semi-rigid layer comprises plastic.

18. The brace of claim 15, wherein the semi-rigid layer comprises a composite material.

19. The brace of claim 15, further comprising a fastener layer disposed between the distal exterior layer and the semi-rigid layer, wherein the distal exterior layer includes at least one cutout that exposes a portion of the fastener layer.

20. The brace of claim 19, wherein the fastener layer is configured such that a portion of at least one strap of the brace may removably attach to a portion of the fastener layer exposed in a cutout of the distal exterior layer.

* * * * *